United States Patent
Sheldon et al.

(10) Patent No.: US 10,207,116 B2
(45) Date of Patent: Feb. 19, 2019

(54) PACING MODE SWITCHING IN A VENTRICULAR PACEMAKER

(71) Applicant: Medtronic, Inc., Minneapolis, MN (US)

(72) Inventors: Todd J Sheldon, North Oaks, MN (US); Yong K Cho, Excelsior, MN (US); Wade M Demmer, Coon Rapids, MN (US); Mark K Erickson, Brooklyn Park, MN (US); Vincent E Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/366,993

(22) Filed: Dec. 1, 2016

(65) Prior Publication Data
US 2018/0154154 A1    Jun. 7, 2018

(51) Int. Cl.
| | | |
|---|---|---|
| *A61N 1/368* | (2006.01) | |
| *A61N 1/365* | (2006.01) | |
| *A61N 1/375* | (2006.01) | |
| *A61N 1/372* | (2006.01) | |

(52) U.S. Cl.
CPC ....... *A61N 1/3688* (2013.01); *A61N 1/36535* (2013.01); *A61N 1/36542* (2013.01); *A61N 1/36578* (2013.01); *A61N 1/3756* (2013.01); *A61N 1/37205* (2013.01)

(58) Field of Classification Search
CPC .............. A61N 1/3688; A61N 1/36542; A61N 1/36535
See application file for complete search history.

(56) References Cited

U.S. PATENT DOCUMENTS

| | | | |
|---|---|---|---|
| 4,485,813 A | | 12/1984 | Anderson et al. |
| 4,559,947 A | * | 12/1985 | Renger .............. A61N 1/37223 607/15 |
| 4,846,195 A | * | 7/1989 | Alt ...................... A61N 1/36542 600/595 |
| 5,052,388 A | | 10/1991 | Sivula et al. |
| 5,065,759 A | | 11/1991 | Begemann et al. |

(Continued)

FOREIGN PATENT DOCUMENTS

| | | |
|---|---|---|
| WO | 2016014352 A1 | 1/2016 |
| WO | 2016064663 A1 | 4/2016 |
| WO | 2016094175 A1 | 6/2016 |

OTHER PUBLICATIONS

U.S. Appl. No. 14/964,279, filed Apr. 23, 2015.

(Continued)

*Primary Examiner* — William J Levicky

(57) ABSTRACT

An intracardiac ventricular pacemaker is configured to operate in in a selected one of an atrial-tracking ventricular pacing mode and a non-atrial tracking ventricular pacing mode. A control circuit of the pacemaker determines at least one motion signal metric from the motion signal, compares the at least one motion signal metric to pacing mode switching criteria; and responsive to the pacing mode switching criteria being satisfied, switches from the selected one of the non-atrial tracking pacing mode and the atrial tracking pacing mode to the other one of the non-atrial tracking pacing mode and the atrial tracking pacing mode for controlling ventricular pacing pulses delivered by the pacemaker.

29 Claims, 14 Drawing Sheets

(56) References Cited

U.S. PATENT DOCUMENTS

| | | | |
|---|---|---|---|
| 5,144,949 | A | 9/1992 | Olson |
| 5,312,445 | A | 5/1994 | Nappholz et al. |
| 5,480,412 | A | 1/1996 | Mouchawar et al. |
| 5,496,361 | A | 3/1996 | Moberg et al. |
| 5,507,782 | A | 4/1996 | Kieval et al. |
| 5,562,711 | A | 10/1996 | Yerich et al. |
| 5,593,431 | A * | 1/1997 | Sheldon ............ A61N 1/36542 607/19 |
| 5,683,432 | A | 11/1997 | Goedeke et al. |
| 5,720,769 | A | 2/1998 | van Oort et al. |
| 5,836,987 | A | 11/1998 | Baumann et al. |
| 5,861,011 | A | 1/1999 | Stoop |
| 5,885,471 | A | 3/1999 | Ruben et al. |
| 6,044,297 | A | 3/2000 | Sheldon et al. |
| 6,295,471 | B1 * | 9/2001 | Bornzin ............... A61N 1/3712 607/28 |
| 6,650,940 | B1 | 11/2003 | Zhu et al. |
| 6,738,669 | B1 | 5/2004 | Sloman et al. |
| 6,904,315 | B2 | 6/2005 | Panken et al. |
| 7,031,772 | B2 | 4/2006 | Condie et al. |
| 7,062,328 | B1 * | 6/2006 | Levine .................. A61N 1/362 607/27 |
| 7,127,289 | B2 | 10/2006 | Yu et al. |
| 7,130,681 | B2 | 10/2006 | Gebhardt et al. |
| 7,200,437 | B1 | 4/2007 | Nabutovsky et al. |
| 7,565,195 | B1 | 7/2009 | Kroll et al. |
| 7,630,767 | B1 | 12/2009 | Poore et al. |
| 7,634,313 | B1 | 12/2009 | Kroll et al. |
| 7,904,155 | B2 | 3/2011 | Yu et al. |
| 8,103,344 | B2 | 1/2012 | Björling |
| 8,214,036 | B2 | 7/2012 | Casset |
| 8,233,980 | B2 | 7/2012 | Pei |
| 8,233,981 | B2 | 7/2012 | Casset |
| 8,433,409 | B2 | 4/2013 | Johnson et al. |
| 8,532,785 | B1 | 9/2013 | Crutchfield et al. |
| 8,541,131 | B2 | 9/2013 | Lund et al. |
| 8,543,204 | B2 | 9/2013 | Demmer et al. |
| 8,792,980 | B2 | 7/2014 | Yu et al. |
| 8,798,745 | B2 | 8/2014 | Jacobson |
| 8,923,963 | B2 | 12/2014 | Bonner et al. |
| 8,996,109 | B2 | 3/2015 | Karst et al. |
| 9,272,146 | B2 | 3/2016 | Anselmi |
| 9,278,218 | B2 | 3/2016 | Karst et al. |
| 9,393,424 | B2 | 7/2016 | Demmer et al. |
| 9,399,139 | B2 | 7/2016 | Demmer et al. |
| 9,399,140 | B2 | 7/2016 | Cho et al. |
| 9,427,594 | B1 | 8/2016 | Bomzin et al. |
| 9,724,518 | B2 | 8/2017 | Sheldon et al. |
| 9,775,982 | B2 | 10/2017 | Grubac et al. |
| 9,814,887 | B2 | 11/2017 | Nikolski et al. |
| 2012/0067490 | A1 | 3/2012 | Duval et al. |
| 2012/0095521 | A1 | 4/2012 | Hintz |
| 2012/0172892 | A1 | 7/2012 | Grubac et al. |
| 2012/0221068 | A1 | 8/2012 | Ellingson |
| 2013/0123872 | A1 | 5/2013 | Bornzin et al. |
| 2013/0138006 | A1 | 5/2013 | Bornzin et al. |
| 2013/0325081 | A1 | 12/2013 | Karst et al. |
| 2014/0042482 | A1 | 2/2014 | Kim et al. |
| 2014/0121721 | A1 | 5/2014 | Ghanem et al. |
| 2015/0217119 | A1 | 8/2015 | Nikolski et al. |
| 2015/0224315 | A1 | 8/2015 | Stahmann |
| 2015/0335894 | A1 | 11/2015 | Bomzin et al. |
| 2016/0011416 | A1 | 1/2016 | Kobayashi |
| 2016/0015287 | A1 | 1/2016 | Anderson et al. |
| 2016/0015322 | A1 | 1/2016 | Anderson et al. |
| 2016/0015984 | A1 | 1/2016 | Demmer et al. |
| 2016/0015985 | A1 | 1/2016 | Cho et al. |
| 2016/0023000 | A1 * | 1/2016 | Cho .................... A61N 1/36578 607/18 |
| 2016/0067486 | A1 | 3/2016 | Brown et al. |
| 2016/0067487 | A1 | 3/2016 | Demmer et al. |
| 2016/0067490 | A1 | 3/2016 | Carney et al. |
| 2016/0067500 | A1 | 3/2016 | Demmer et al. |
| 2016/0114162 | A1 | 4/2016 | Sheldon et al. |
| 2016/0114168 | A1 | 4/2016 | Demmer et al. |
| 2016/0114169 | A1 | 4/2016 | Sheldon et al. |
| 2016/0129261 | A1 | 5/2016 | Demmer et al. |
| 2016/0129263 | A1 | 5/2016 | Demmer et al. |
| 2016/0144190 | A1 | 5/2016 | Cao et al. |
| 2016/0144191 | A1 | 5/2016 | Sheldon |
| 2016/0167487 | A1 | 6/2016 | Tamarapoo et al. |
| 2016/0250478 | A1 | 9/2016 | Greenhut et al. |
| 2018/0028814 | A1 | 2/2018 | Ghosh |

OTHER PUBLICATIONS

U.S. Appl. No. 14/920,228, filed Oct. 22, 2015.
U.S. Appl. No. 14/810,559, filed Jul. 28, 2015.
U.S. Appl. No. 15/280,538, filed Sep. 29, 2016.
U.S. Appl. No. 15/280,339, filed Sep. 29, 2016.
U.S. Appl. No. 15/342,699, filed Nov. 3, 2016.
U.S. Appl. No. 15/140,585, filed Apr. 28, 2016.
U.S. Appl. No. 15/221,995, filed Jul. 28, 2016.
U.S. Appl. No. 15/222,302, filed Jul. 28, 2016.
U.S. Appl. No. 14/826,396, filed Aug. 14, 2015.
Demmer et al., "Power Management for Implantable Medical Device Systems", U.S. Appl. No. 5/783,573, filed Oct. 13, 2017, 41 pages.
(PCT/US2017/064129) PCT Notification of Transmittal of the International Search Report and the Written Opinion of the International Searching Authority, dated Feb. 22, 2018, 13 pages.

* cited by examiner

PACING MODE SWITCHING IN A VENTRICULAR PACEMAKER

TECHNICAL FIELD

The disclosure relates to a ventricular pacemaker and associated method for switching between an atrial tracking ventricular pacing mode and a non-atrial tracking ventricular pacing mode based on a motion sensor signal.

BACKGROUND

Implantable cardiac pacemakers are often placed in a subcutaneous pocket and coupled to one or more transvenous medical electrical leads carrying pacing and sensing electrodes positioned in the heart. A cardiac pacemaker implanted subcutaneously may be a single chamber pacemaker coupled to one transvenous medical lead for positioning electrodes in one heart chamber, atrial or ventricular, or a dual chamber pacemaker coupled to two intracardiac leads for positioning electrodes in both an atrial and a ventricular chamber. Multi-chamber pacemakers are also available that may be coupled to three leads, for example, for positioning electrodes for pacing and sensing in one atrial chamber and both the right and left ventricles.

Intracardiac pacemakers have recently been introduced that are implantable within a ventricular chamber of a patient's heart for delivering ventricular pacing pulses. Such a pacemaker may sense R-wave signals attendant to intrinsic ventricular depolarizations and deliver ventricular pacing pulses in the absence of sensed R-waves. While single chamber ventricular sensing and pacing by an intracardiac ventricular pacemaker may adequately address some patient conditions, other conditions may require atrial and ventricular (dual chamber) sensing for providing atrial-synchronized ventricular pacing in order to maintain a regular heart rhythm.

SUMMARY

In general, the disclosure is directed to a ventricular pacemaker and techniques for controlling the ventricular pacing mode by switching between an atrial tracking pacing mode and a non-atrial tracking pacing mode. The ventricular pacemaker may be an intracardiac pacemaker and may be configured to detect atrial systolic events from a motion signal produced by a motion sensor included in the intracardiac ventricular pacemaker. The ventricular pacemaker, operating according to the techniques disclosed herein, automatically switches between an atrial tracking pacing mode and a non-atrial tracking pacing mode according to mode-switching criteria in order to provide an appropriate ventricular pacing rate that supports the patient's metabolic need.

In one example, the disclosure provides an intracardiac ventricular pacemaker including a pulse generator, a motion sensor, and a control circuit. The pulse generator is configured to generate and deliver pacing pulses to a ventricle of a patient's heart via electrodes coupled to the pacemaker. The motion sensor is configured to produce a motion signal. The control circuit is coupled to the motion sensor and the pulse generator and is configured to operate in a selected one of either an atrial-tracking ventricular pacing mode or a non-atrial tracking ventricular pacing mode, determine at least one motion signal metric from the motion signal, compare the at least one motion signal metric to pacing mode switching criteria; and responsive to the pacing mode switching criteria being satisfied, switch from the selected one of the non-atrial tracking pacing mode and the atrial tracking pacing mode to the other one of the non-atrial tracking pacing mode and the atrial tracking pacing mode for controlling the pacing pulses delivered by the pulse generator.

In another example, the disclosure provides a method performed by an intracardiac ventricular pacemaker having a motion sensor configured to produce a motion signal. The pacemaker is capable of operating in an atrial tracking pacing mode and in a non-atrial tracking pacing mode. The method includes operating in a selected one of either an atrial-tracking ventricular pacing mode or a non-atrial tracking ventricular pacing mode; determining by a control circuit of the pacemaker at least one motion signal metric from the motion signal; comparing the at least one motion signal metric to pacing mode switching criteria; and responsive to the pacing mode switching criteria being satisfied, switching from the selected one of the non-atrial tracking pacing mode and the atrial tracking pacing mode to the other one of the non-atrial tracking pacing mode and the atrial tracking pacing mode for controlling ventricular pacing pulses delivered by the pacemaker.

In another example, the disclosure provides a non-transitory, computer-readable medium storing a set of instructions, which, when executed by a control circuit of an intracardiac ventricular pacemaker having a motion sensor configured to produce a motion signal, cause the pacemaker to operate in a selected one of either an atrial-tracking ventricular pacing mode or a non-atrial tracking ventricular pacing mode; determine at least one motion signal metric from the motion signal; compare the at least one motion signal metric to pacing mode switching criteria; and responsive to the pacing mode switching criteria being satisfied, switch from the selected one of the non-atrial tracking pacing mode and the atrial tracking pacing mode to the other one of the non-atrial tracking pacing mode and the atrial tracking pacing mode for controlling ventricular pacing pulses delivered by the pacemaker.

This summary is intended to provide an overview of the subject matter described in this disclosure. It is not intended to provide an exclusive or exhaustive explanation of the apparatus and methods described in detail within the accompanying drawings and description below. Further details of one or more examples are set forth in the accompanying drawings and the description below.

DETAILED DESCRIPTION

During atrial-synchronized ventricular pacing, ventricular pacing pulses are delivered at an atrioventricular (AV) pacing interval following an atrial event to provide proper synchrony between the atrial contraction and the ventricular contraction. In order for an intraventricular pacemaker to provide atrial-synchronized ventricular pacing, the intraventricular pacemaker needs to sense or detect the atrial event to start the AV pacing interval. As the atrial rate increases or decreases, the ventricular pacing rate tracks the atrial rate. This atrial synchronized ventricular pacing is referred to as an "atrial-tracking" pacing mode. In a non-atrial tracking ventricular pacing mode, the ventricular pacing pulses are delivered at a ventricular lower rate (LR) pacing interval that is independent of atrial events and does not track the atrial rate. Generally, an atrial tracking ventricular pacing mode is desirable when the sinus node of the heart is functioning normally in setting the intrinsic atrial rate or the atria are being paced at an appropriate pacing rate for the patient's level of physical activity.

Under some circumstances, however, it is undesirable to track the atrial rate, e.g., during atrial tachyarrhythmia such as atrial fibrillation or atrial flutter. As such, a method for switching between an atrial tracking ventricular pacing mode and a non-atrial tracking ventricular pacing mode is required to enable an intracardiac ventricular pacemaker to deliver ventricular pacing that tracks the atrial rate at appropriate times and does not track the atrial rate at other times, based on the patient's need for ventricular pacing and in a manner that does not result in pacemaker mediated ventricular tachycardia.

Techniques are disclosed herein for controlling switching between an atrial tracking ventricular pacing mode and a non-atrial tracking ventricular pacing mode in an intraventricular pacemaker. The intraventricular pacemaker has a motion sensor for detecting atrial systolic mechanical events. During the atrial tracking pacing mode, the AV pacing interval is started in response to detecting the atrial systolic mechanical event. Atrial systolic mechanical event detection during both the atrial tracking mode and the non-atrial tracking mode may be used to determine if pacing mode switching criteria are met for controlling when the pacemaker switches between the atrial tracking pacing mode and the non-atrial tracking pacing mode.

Figure 1:
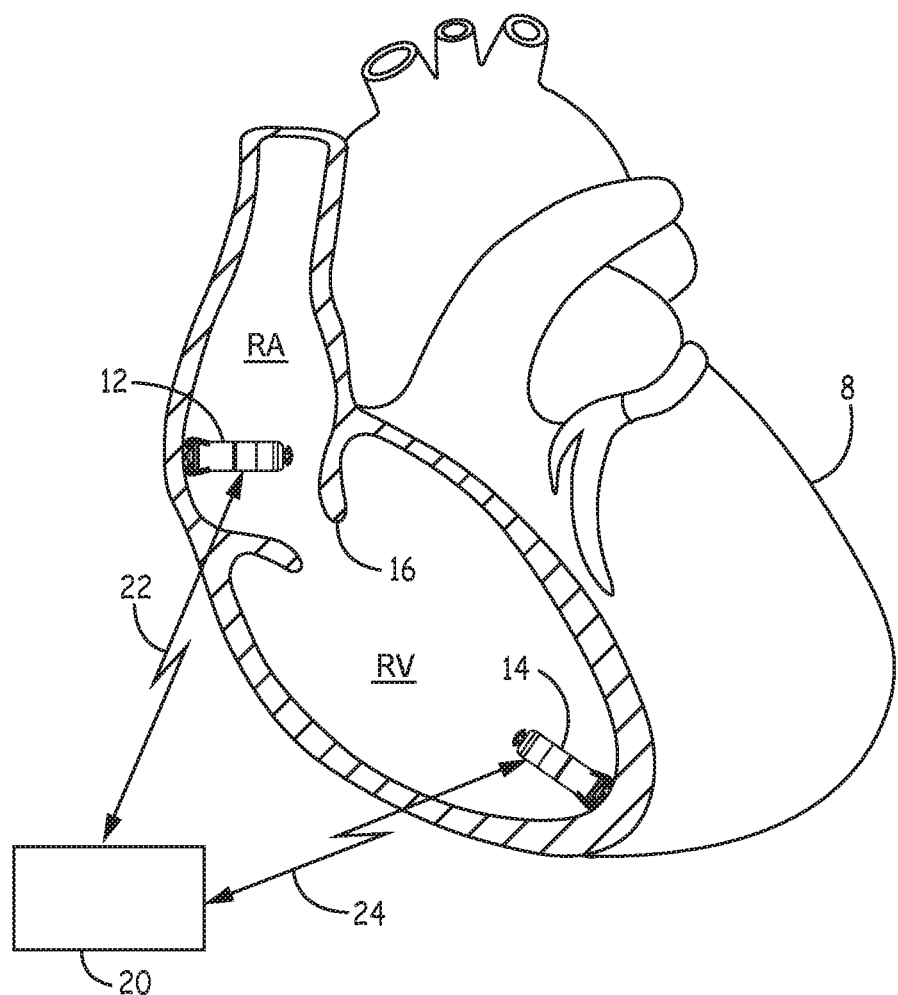
FIG. 1 is a conceptual diagram illustrating an intracardiac pacing system that may be used to sense cardiac electrical signals and motion signals induced by cardiac motion and flowing blood and provide pacing therapy to a patient's heart.

FIG. 1 is a conceptual diagram illustrating an intracardiac pacing system 10 that may be used to sense cardiac electrical signals and motion signals induced by cardiac motion and flowing blood and provide pacing therapy to a patient's heart 8. IMD system 10 includes a right ventricular (RV) intracardiac pacemaker 14 and may optionally include a right atrial (RA) intracardiac pacemaker 12 in some examples. Pacemakers 12 and 14 are transcatheter intracardiac pacemakers which may be adapted for implantation wholly within a heart chamber, e.g., wholly within the RV, wholly within the left ventricle (LV), wholly within the RA or wholly within the left atrium (LA) of heart 8.

In the example of FIG. 1, pacemaker 12 is positioned along an endocardial wall of the RA, e.g., along the RA lateral wall or RA septum. Pacemaker 14 is positioned along an endocardial wall of the RV, e.g., near the RV apex though other locations are possible. The techniques disclosed herein are not limited to the pacemaker locations shown in the example of FIG. 1 and other positions and relative locations in the heart 8 and from each other are possible. For example, a ventricular intracardiac pacemaker 14 may be positioned in the LV for and configured to detect cardiac motion signals and deliver atrial-synchronized ventricular pacing to the LV using the techniques disclosed herein.

Pacemakers 12 and 14 are reduced in size compared to subcutaneously implanted pacemakers and may be generally cylindrical in shape to enable transvenous implantation via a delivery catheter. In other examples, pacemakers 12 and 14 may be positioned at any other location inside heart 8. For example, pacemaker 12 may be positioned outside or within the right atrium or left atrium to provide respective right atrial or left atrial pacing. Pacemaker 14 may be positioned within the right ventricle or left ventricle to provide respective right ventricular or left ventricular pacing and for sensing motion signals by a motion sensor within the ventricular chamber.

Pacemakers 12 and 14 are each capable of producing electrical stimulation pulses, e.g., pacing pulses, delivered to heart 8 via one or more electrodes on the outer housing of the pacemaker. RA pacemaker 12 is configured to sense a cardiac electrical signal from within the RA that may be used to produce an RA intracardiac electrogram (EGM) signal. RV pacemaker 14 is configured to deliver RV pacing pulses and sense an RV cardiac electrical signal using housing based electrodes for producing an RV EGM signal. The cardiac electrical signals may be sensed by the respective pacemaker 12 or 14 using the housing based electrodes that are also used to deliver pacing pulses to the respective RA or RV.

In some examples, a patient may only require RV pacemaker 14 for delivering ventricular pacing. In other examples, depending on individual patient need, RA pacemaker 12 may be required for delivering atrial pacing. The RV pacemaker 14 is configured to control the delivery of ventricular pacing pulses to the RV in a manner that promotes synchrony between the RA activation and the RV activation, e.g., by maintaining a target AV pacing interval between atrial events and ventricular pacing pulses. That is, the RV pacemaker 14 controls RV pacing pulse delivery to maintain a desired AV interval between atrial activations (intrinsic or pacing-evoked) corresponding to atrial systole and ventricular pacing pulses delivered to cause ventricular depolarization.

According to the techniques described herein, atrial activations are detected by RV pacemaker 14 from a motion sensor signal that includes motion signals caused by ventricular and atrial events. For example, acceleration of blood flowing into the RV through the tricuspid valve 16 between the RA and RV caused by atrial activation, sometimes referred to as the "atrial kick," is detected by RV pacemaker 14 from the signal produced by a motion sensor, for example an accelerometer, included in RV pacemaker 14. Other motion signals detected by RV pacemaker 14, such as motion caused by ventricular contraction, motion caused by ventricular relaxation, and motion caused by passive filling of the ventricle are described below in conjunction with FIG. 4.

Atrial P-waves that are attendant to atrial depolarization are relatively low amplitude signals in the near-field RV cardiac electrical signal received by pacemaker 14 (e.g., compared to the near-field R-wave) and therefore can be difficult to reliably detect from the cardiac electrical signal acquired by RV pacemaker 14. As such, atrial-synchronized ventricular pacing by RV pacemaker 14 may not be reliable when based solely on a cardiac electrical signal received by RV pacemaker 14. According to the techniques disclosed herein, the RV pacemaker 14 includes a motion sensor, such as an accelerometer, and is configured to detect an atrial event corresponding to atrial mechanical activation or atrial systole using a signal from the motion sensor. Ventricular pacing pulses are synchronized to the atrial event that is detected from the accelerometer signal by setting a programmable atrioventricular (AV) pacing interval that controls the timing of the ventricular pacing pulse relative to the detected atrial systolic event. As described below, detection of the atrial systolic event used to synchronize ventricular pacing pulses to atrial systole may include detection of other cardiac event motion signals in order to positively identify the atrial systolic event.

A target AV interval may be a programmed value selected by a clinician and is the time interval from the detection of the atrial event until delivery of the ventricular pacing pulse. In some instances, the target AV interval may be started from the time the atrial systolic event is detected based on a motion sensor signal or starting from an identified fiducial point of the atrial systolic event signal. The target AV interval may be identified as being hemodynamically optimal for a given patient based on clinical testing or assessments of the patient or based on clinical data from a population of patients. The target AV interval may be determined to be optimal based on relative timing of electrical and mechanical events as identified from the cardiac electrical signal received by RV pacemaker 14 and the motion sensor signal received by RV pacemaker 14.

Pacemakers 12 and 14 may each be capable of bidirectional wireless communication with an external device 20 for programming the AV pacing interval and other pacing control parameters as well as mechanical event sensing parameters utilized for detecting ventricular mechanical events and the atrial systolic event from the motion sensor signal. Aspects of external device 20 may generally correspond to the external programming/monitoring unit disclosed in U.S. Pat. No. 5,507,782 (Kieval, et al.), hereby incorporated herein by reference in its entirety. External device 20 is often referred to as a "programmer" because it is typically used by a physician, technician, nurse, clinician or other qualified user for programming operating parameters in pacemakers 12 and 14. External device 20 may be located in a clinic, hospital or other medical facility. External device 20 may alternatively be embodied as a home monitor or a handheld device that may be used in a medical facility, in the patient's home, or another location. Operating parameters, including sensing and therapy delivery control parameters and pacing mode switching criteria, may be programmed into pacemaker 14 using external device 20.

External device 20 is configured for bidirectional communication with implantable telemetry circuitry included in RV pacemaker 14 and RA pacemaker 12 (when present). External device 20 establishes a wireless radio frequency (RF) communication link 22 with RA pacemaker 12 and wireless RF communication link 24 with RV pacemaker 14 using a communication protocol that appropriately addresses the targeted pacemaker 12 or 14. Communication links 22 and 24 may be established using an RF link such as BLUETOOTH®, Wi-Fi, Medical Implant Communication Service (MICS) or other communication bandwidth. In some examples, external device 20 may include a programming head that is placed proximate pacemaker 12 or 14 to establish and maintain a communication link, and in other examples external device 20 and pacemakers 12 and 14 may be configured to communicate using a distance telemetry algorithm and circuitry that does not require the use of a programming head and does not require user intervention to maintain a communication link. An example RF telemetry communication system that may be implemented in system 10 is generally disclosed in U.S. Pat. No. 5,683,432 (Goedeke, et al.), hereby incorporated herein by reference in its entirety.

External device 20 may display data and information relating to pacemaker functions to a user for reviewing pacemaker operation and programmed parameters as well as EGM signals transmitted from pacemaker 14 or pacemaker 12, motion sensor signals acquired by pacemaker 14, or other physiological data that is acquired by and retrieved from pacemakers 12 and/or 14 during an interrogation session.

It is contemplated that external device 20 may be in wired or wireless connection to a communications network via a telemetry circuit that includes a transceiver and antenna or via a hardwired communication line for transferring data to a remote database or computer to allow remote management of the patient. Remote patient management systems including a remote patient database may be configured to utilize the presently disclosed techniques to enable a clinician to review EGM, motion sensor, and marker channel data and authorize programming of sensing and therapy control parameters in RV pacemaker 14, e.g., after viewing a visual representation of EGM, motion sensor signal and marker channel data.

Pacemaker 12 and pacemaker 14 may or may not be configured to communicate directly with each other. When pacemakers 12 and 14 are configured to communicate with each other, communication may be minimized in order to conserve battery life of the intracardiac pacemakers 12 and 14. As such, communication may not occur on a beat-by-beat basis between the RA pacemaker 12 and RV pacemaker 14 for communicating when the other pacemaker is sensing cardiac events or when it is delivering pacing pulses. As disclosed herein, RV pacemaker 14, however, is configured to detect atrial events as often as beat-by-beat from a motion sensor signal, without requiring communication signals from RA pacemaker 12 to provide atrial event detection for controlling atrial-synchronized ventricular pacing and for determining when to switch to a non-atrial tracking pacing mode.

Figure 2A:
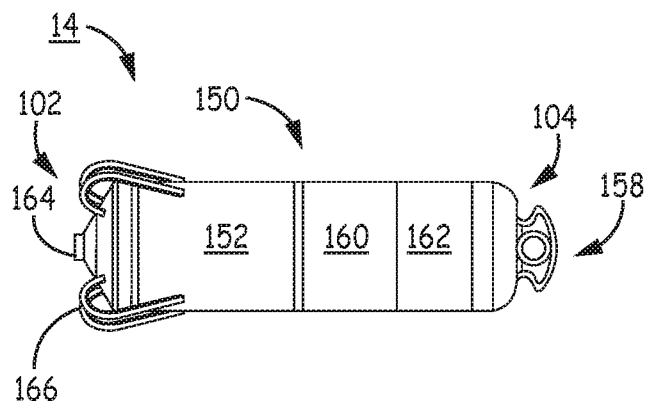
FIG. 2A is a conceptual diagram of the intracardiac ventricular pacemaker shown in FIG. 1.

FIG. 2A is a conceptual diagram of the intracardiac RV pacemaker 14 shown in FIG. 1. RV pacemaker 14 includes electrodes 162 and 164 spaced apart along the housing 150 of pacemaker 14 for sensing cardiac electrical signals and delivering pacing pulses. Electrode 164 is shown as a tip electrode extending from a distal end 102 of pacemaker 14, and electrode 162 is shown as a ring electrode along a mid-portion of housing 150, for example adjacent proximal end 104. Distal end 102 is referred to as "distal" in that it is expected to be the leading end as pacemaker 14 is advanced through a delivery tool, such as a catheter, and placed against a targeted pacing site.

Electrodes 162 and 164 form an anode and cathode pair for bipolar cardiac pacing and sensing. In alternative embodiments, pacemaker 14 may include two or more ring electrodes, two tip electrodes, and/or other types of electrodes exposed along pacemaker housing 150 for delivering electrical stimulation to heart 8 and sensing cardiac electrical signals. Electrodes 162 and 164 may be, without limitation, titanium, platinum, iridium or alloys thereof and may include a low polarizing coating, such as titanium nitride, iridium oxide, ruthenium oxide, platinum black among others. Electrodes 162 and 164 may be positioned at locations along pacemaker 14 other than the locations shown.

Housing 150 is formed from a biocompatible material, such as a stainless steel or titanium alloy. In some examples, the housing 150 may include an insulating coating. Examples of insulating coatings include parylene, urethane, PEEK, or polyimide among others. The entirety of the housing 150 may be insulated, but only electrodes 162 and 164 uninsulated. Electrode 164 may serve as a cathode electrode and be coupled to internal circuitry, e.g., a pacing pulse generator and cardiac electrical signal sensing circuitry, enclosed by housing 150 via an electrical feedthrough crossing housing 150. Electrode 162 may be formed as a conductive portion of housing 150 as a ring electrode that is electrically isolated from the other portions of the housing 150 as generally shown in FIG. 2A. In other examples, the entire periphery of the housing 150 may function as an electrode that is electrically isolated from tip electrode 164, instead of providing a localized ring electrode such as anode electrode 162. Electrode 162 formed along an electrically conductive portion of housing 150 serves as a return anode during pacing and sensing.

The housing 150 includes a control electronics subassembly 152, which houses the electronics for sensing cardiac signals, producing pacing pulses and controlling therapy delivery and other functions of pacemaker 14 as described below in conjunction with FIG. 3. A motion sensor may be implemented as an accelerometer enclosed within housing 150 in some examples. The accelerometer provides a signal to a processor included in control electronics subassembly 152 for signal processing and analysis for detecting ventricular mechanical events and atrial systolic events for timing ventricular pacing pulses as described below.

Housing 150 further includes a battery subassembly 160, which provides power to the control electronics subassembly 152. Battery subassembly 160 may include features of the batteries disclosed in commonly-assigned U.S. Pat. No. 8,433,409 (Johnson, et al.) and U.S. Pat. No. 8,541,131 (Lund, et al.), both of which are hereby incorporated by reference herein in their entirety.

Pacemaker 14 may include a set of fixation tines 166 to secure pacemaker 14 to patient tissue, e.g., by actively engaging with the ventricular endocardium and/or interacting with the ventricular trabeculae. Fixation tines 166 are configured to anchor pacemaker 14 to position electrode 164 in operative proximity to a targeted tissue for delivering therapeutic electrical stimulation pulses. Numerous types of active and/or passive fixation members may be employed for anchoring or stabilizing pacemaker 14 in an implant position. Pacemaker 14 may include a set of fixation tines as disclosed in commonly-assigned, U.S. Pat. No. 9,775,982 (Grubac, et al.), hereby incorporated herein by reference in its entirety.

Pacemaker 14 may optionally include a delivery tool interface 158. Delivery tool interface 158 may be located at the proximal end 104 of pacemaker 14 and is configured to connect to a delivery device, such as a catheter, used to position pacemaker 14 at an implant location during an implantation procedure, for example within a heart chamber.

Figure 2B:
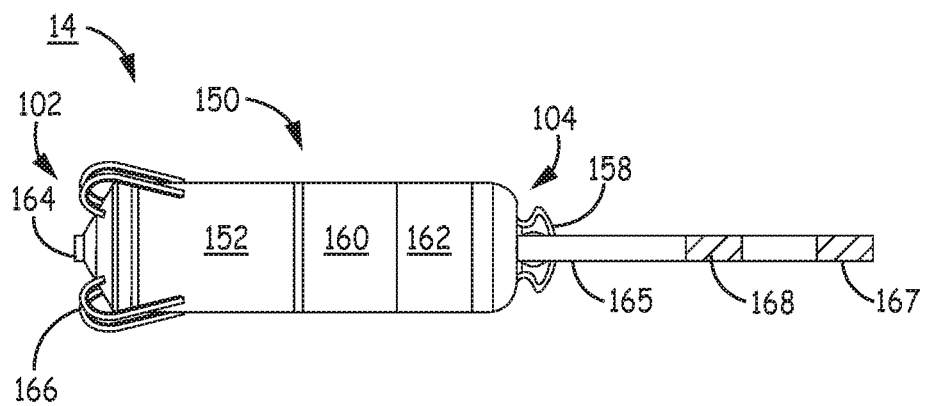
FIG. 2B is a conceptual diagram of another example of the intracardiac ventricular pacemaker shown in FIG. 1.

FIG. 2B is a conceptual diagram of another example of RV pacemaker 14. In FIG. 2B, RV pacemaker 14 includes a proximal sensing extension 165 extending away from housing 150 and carrying a pair of sensing electrodes 167 and 168. The proximal sensing extension 165 may be coupled to the housing 150 for positioning a return sensing electrode 168 or 167 which may be paired with distal electrode 164 at an increased inter-electrode distance compared to the inter-electrode spacing of housing-based electrodes 162 and 164. The increased inter-electrode distance may facilitate sensing of far-field atrial signals such as P-waves attendant to atrial depolarization.

Alternatively, electrodes 167 and 168 may form a sensing electrode pair for sensing atrial P-waves. When distal end 102 is fixed along the RV apex, sensing extension 165 may extend toward the RA thereby positioning electrodes 167 and 168 nearer the atrial tissue for sensing far-field atrial P-waves. One electrode 167 may be coupled to sensing circuitry enclosed in housing 150 via an electrical feedthrough crossing housing 150, and one electrode 168 may be coupled to housing 150 to serve as a ground electrode.

Figure 3:
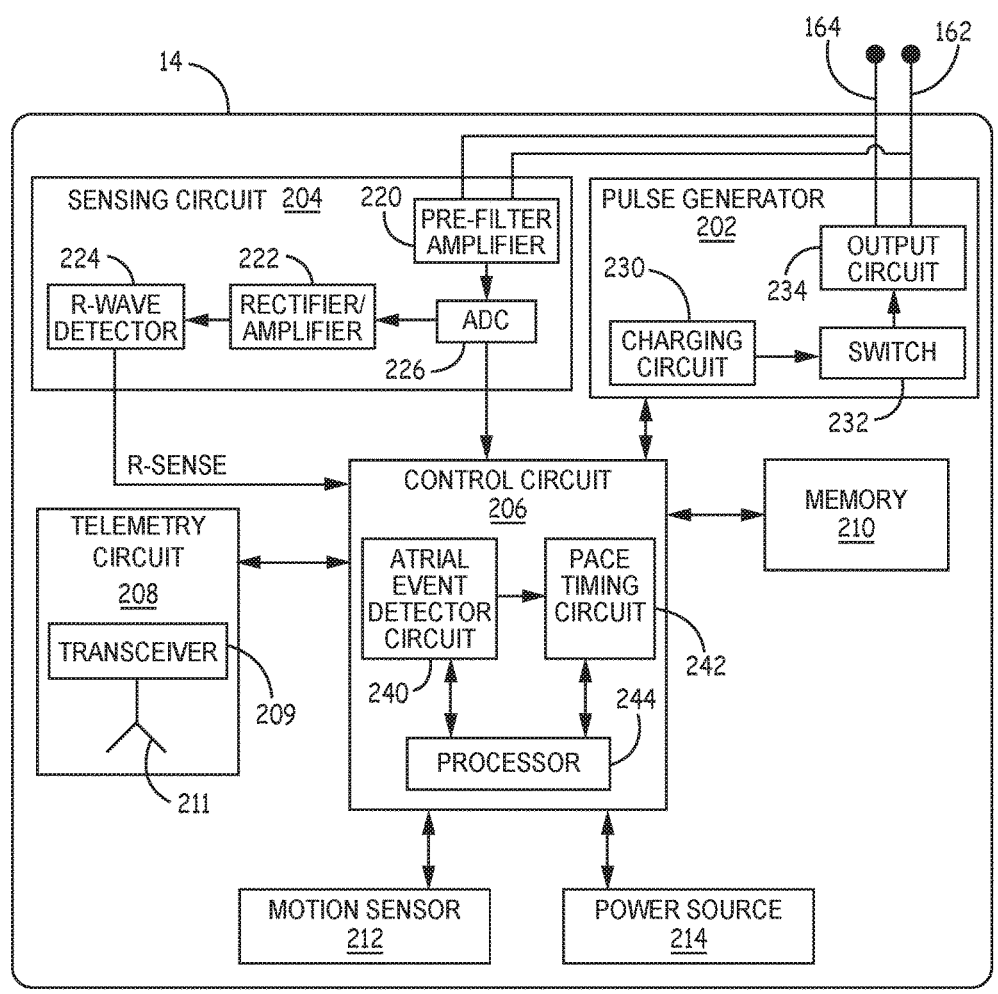
FIG. 3 is a schematic diagram of an example configuration of the pacemaker of FIG. 2A.

FIG. 3 is a schematic diagram of an example configuration of pacemaker 14 shown in FIG. 1. Pacemaker 14 includes a pulse generator 202, a sensing circuit 204, a control circuit 206, memory 210, telemetry circuit 208, motion sensor 212 and a power source 214. Motion sensor 212 is implemented as an accelerometer in the examples described herein and may also be referred to herein as "accelerometer 212." Motion sensor 212 is not limited to being an accelerometer, however, and other motion sensors may be utilized successfully in pacemaker 14 for detecting cardiac motion signals according to the techniques described herein. Examples of motion sensors that may be implemented in pacemaker 14 include piezoelectric sensors and micro electro-mechanical systems (MEMS) devices.

Motion sensor 212 may be a multi-axis sensor, e.g., a two-dimensional or three-dimensional sensor, with each axis providing a signal that may be analyzed individually or in combination for detecting cardiac mechanical events. Motion sensor 212 produces an electrical signal correlated to motion or vibration of sensor 212 (and pacemaker 14), e.g., when subjected to flowing blood and cardiac motion. Motion sensor 212 may be a one-dimensional, single axis accelerometer, two-dimensional or three-dimensional multi-axis accelerometer. One example of an accelerometer for use in implantable medical devices is generally disclosed in U.S. Pat. No. 5,885,471 (Ruben, et al.), incorporated herein by reference in its entirety. An implantable medical device arrangement including a piezoelectric accelerometer for detecting patient motion is disclosed, for example, in U.S. Pat. No. 4,485,813 (Anderson, et al.) and U.S. Pat. No. 5,052,388 (Sivula, et al.), both of which patents are hereby incorporated by reference herein in their entirety. Examples of three-dimensional accelerometers that may be implemented in pacemaker 14 and used for detecting cardiac mechanical events using the presently disclosed techniques are generally described in U.S. Pat. No. 5,593,431 (Sheldon) and U.S. Pat. No. 6,044,297 (Sheldon), both of which are incorporated herein by reference in their entirety. Other accelerometer designs may be used for producing an electrical signal that is correlated to motion imparted on pacemaker 14 due to ventricular and atrial events.

In addition to being subjected to cardiac motion, the motion sensor 212 is subjected to patient body motion during physical activity such as walking, driving, exercise, changing body posture, household chores and other activities of daily living. The motion sensor signal may be used by control circuit 206 for detecting cardiac mechanical events as described in greater detail below as well as determining the patient's body posture and/or the level of patient physical activity (e.g., resting, non-resting but within a range of normal activities of daily living, sub-maximal exercise or maximal exercise). Techniques for monitoring patient body posture and patient physical activity from an accelerometer signal are generally disclosed in the above-incorporated references.

The various circuits represented in FIG. 3 may be combined on one or more integrated circuit boards which include a specific integrated circuit (ASIC), an electronic circuit, a processor (shared, dedicated, or group) and memory that execute one or more software or firmware programs, a combinational logic circuit, state machine or other suitable components that provide the described functionality.

Sensing circuit 204 is configured to receive a cardiac electrical signal via electrodes 162 and 164 by a pre-filter and amplifier circuit 220. Pre-filter and amplifier circuit may include a high pass filter to remove DC offset, e.g., a 2.5 to 5 Hz high pass filter, or a wideband filter having a passband of 2.5 Hz to 100 Hz to remove DC offset and high frequency noise. Pre-filter and amplifier circuit 220 may further include an amplifier to amplify the "raw" cardiac electrical signal passed to analog-to-digital converter (ADC) 226. ADC 226 may pass a multi-bit, digital electrogram (EGM) signal to control circuit 206 for use by atrial event detector circuit 240 in identifying ventricular electrical events (e.g., R-waves or T-waves) and/or atrial electrical events, e.g., P-waves. Identification of cardiac electrical events may be used in algorithms for detecting atrial systolic events from the motion sensor signal. The digital signal from ADC 226 may be passed to rectifier and amplifier circuit 222, which may include a rectifier, bandpass filter, and amplifier for passing a cardiac signal to R-wave detector 224.

R-wave detector 224 may include a sense amplifier or other detection circuitry that compares the incoming rectified, cardiac electrical signal to an R-wave detection threshold, which may be an auto-adjusting threshold. When the incoming signal crosses the R-wave detection threshold, the R-wave detector 224 produces an R-wave sensed event signal (R-sense) that is passed to control circuit 206. In other examples, R-wave detector 224 may receive the digital output of ADC 226 for detecting R-waves by a comparator, morphological signal analysis of the digital EGM signal or other R-wave detection techniques. R-wave sensed event signals passed from R-wave detector 224 to control circuit 206 may be used for scheduling ventricular pacing pulses by pace timing circuit 242 and for use in identifying the timing of ventricular electrical events in algorithms performed by atrial event detector circuit 240 for detecting atrial systolic events from a signal received from motion sensor 212.

Control circuit 206 includes an atrial event detector circuit 240, pace timing circuit 242, and processor 244. Atrial event detector circuit 240 is configured to detect atrial mechanical events from a signal received from motion sensor 212. As described below, one or more ventricular mechanical events may be detected from the motion sensor signal in a given cardiac cycle to facilitate positive detection of the atrial systolic event from the motion sensor signal during the ventricular cycle.

Control circuit 206 may receive R-wave sensed event signals and/or digital cardiac electrical signals from sensing circuit 204 for use in detecting and confirming cardiac events and controlling ventricular pacing. For example, R-wave sensed event signals may be passed to pace timing circuit 242 for inhibiting scheduled ventricular pacing pulses or scheduling ventricular pacing pulses when pacemaker 14 is operating in a non-atrial tracking ventricular pacing mode. R-wave sensed event signals may also be passed to atrial event detector circuit 240 for use in setting ventricular event detection windows and/or atrial event refractory periods, for example as shown and described in conjunction with FIG. 6.

Some R-wave sensed event signals may be caused by premature ventricular contractions (PVCs). Control circuit 206 may be configured to detect PVCs based on the timing of an of R-wave sensed event signal since a preceding R-wave or ventricular pacing pulse and/or based on the R-wave signal morphology. PVCs may be discriminated from normally conducted R-waves to avoid scheduling pacing pulses based on PVCs. As described in conjunction with FIG. 12, a PVC detected during a non-atrial tracking pacing mode may trigger an extension of the LR pacing interval to promote atrial systolic event detection from the motion sensor signal during the long compensatory pause following a PVC.

Atrial event detector circuit 240 receives a motion signal from motion sensor 212 and starts an atrial refractory period in response to a ventricular electrical event, e.g., an R-wave sensed event signal from sensing circuit 204 or delivery of a pacing pulse by pulse generator 202. Atrial event detector circuit 240 determines if the motion sensor signal satisfies atrial mechanical systolic event detection criteria outside of the refractory period. The motion sensor signal during the refractory period may be monitored by atrial event detector circuit 240 for the purposes of detecting ventricular mechanical events, which may be used for confirming or validating atrial systolic event detection and/or setting atrial systolic event detection control parameters. As such, ventricular mechanical event detection windows may be set during the atrial refractory period and may be set according to predetermined time intervals following identification of a ventricular electrical event. Atrial event detector circuit 240 may be configured to detect one or more ventricular mechanical events during respective ventricular event detection windows during the atrial refractory period. The timing and detection of the ventricular mechanical events may be used to update the atrial refractory period and/or an atrial systolic detection threshold amplitude and may be used to confirm detection of the atrial systolic event occurring subsequent to expected ventricular mechanical events.

Atrial event detector circuit 240 passes an atrial event detection signal to processor 244 and/or pace timing circuit 242. Pace timing circuit 242 (or processor 244) may additionally receive R-wave sensed event signals from R-wave detector 224 for use in controlling the timing of pacing pulses delivered by pulse generator 202. Processor 244 may include one or more clocks for generating clock signals that are used by pace timing circuit 242 to time out an AV pacing interval that is started upon receipt of an atrial event detection signal from atrial event detector circuit 240. Pace timing circuit 242 may include one or more pacing escape interval timers or counters that are used to time out the AV pacing interval, which may be a programmable interval stored in memory 210 and retrieved by processor 244 for use in setting the AV pacing interval used by pace timing circuit 242. Techniques for controlling atrial-synchronized ventricular pacing using a motion sensor signal are generally disclosed in U.S. Pat. No. 9,399,140, (Yong, et al.), incorporated herein by reference in its entirety.

Pace timing circuit 242 may additionally include a lower rate (LR) pacing interval timer for controlling a minimum ventricular pacing rate in the absence of detected atrial events. For example, if an atrial systolic event is not detected from the motion sensor signal triggering a ventricular pacing pulse at the programmed AV pacing interval, a ventricular pacing pulse may be delivered by pulse generator 202 upon expiration of the LR pacing interval to prevent ventricular asystole and maintain a minimum ventricular rate.

During a non-atrial tracking pacing mode, the LR pacing interval timer is used to control the rate of ventricular pacing pulses that are delivered independent of the atrial rate. The LR pacing interval may be set to a minimum or base LR pacing interval to maintain a minimum ventricular rate and may be adjusted to a temporary LR pacing interval according to provide rate responsive pacing. A sensor indicated rate (SIR) may be determined based on the patient's physical activity level, which may be determined from the motion sensor signal. A temporary LR pacing interval set based on a SIR provides ventricular pacing pulses at a rate greater than the minimum or base pacing rate. The higher ventricular rate support is provided according to the patient's metabolic demand during periods of non-resting physical activity based on the SIR. The use of an accelerometer in an intracardiac pacemaker for obtaining a patient activity signal is generally disclosed in pre-grant U.S. Pat. Publication No. 2015/0217119 A1 filed on Feb. 6, 2014 (Nikolski, et al.), incorporated herein by reference in its entirety. The use of a patient activity signal for determining a SIR and providing rate-responsive pacing is generally disclosed in U.S. Pat. No. 5,720,769 (van Oort) and U.S. Pat. No. 7,031,772 (Condie, et al.), both incorporated herein by reference in its entirety.

Processor 244 may retrieve other programmable pacing control parameters, such as pacing pulse amplitude and pacing pulse width that are passed to pulse generator 202 for controlling pacing pulse delivery. In addition to providing control signals to pace timing circuit 242 and pulse generator 202 for controlling pacing pulse delivery, processor 244 may provide sensing control signals to sensing circuit 204, e.g., R-wave sensing threshold, sensitivity, various blanking and refractory intervals applied to the cardiac electrical signal, and atrial event detection control signals to atrial event detector circuit 240 for use in detecting and confirming atrial systolic events, e.g., ventricular event detection windows, atrial refractory period, detection threshold amplitudes applied to the motion sensor signal, and any other atrial event detection criteria applied by circuitry included in atrial event detector circuit 240.

The functions attributed to pacemaker 14 herein may be embodied as one or more processors, controllers, hardware, firmware, software, or any combination thereof. Depiction of different features as specific circuitry is intended to highlight different functional aspects and does not necessarily imply that such functions must be realized by separate hardware, firmware or software components or by any particular circuit architecture. Rather, functionality associated with one or more circuits described herein may be performed by separate hardware, firmware or software components, or integrated within common hardware, firmware or software components. For example, atrial systolic event detection from the motion sensor signal and ventricular pacing control operations performed by pacemaker 14 may be implemented in control circuit 206 executing instructions stored in memory 210 and relying on input from sensing circuit 204 and motion sensor 212.

The operation of circuitry included in pacemaker 14 as disclosed herein should not be construed as reflective of a specific form of hardware, firmware and software necessary to practice the techniques described. It is believed that the particular form of software, hardware and/or firmware will be determined primarily by the particular system architecture employed in the pacemaker 14 and by the particular sensing and therapy delivery circuitry employed by the pacemaker 14. Providing software, hardware, and/or firmware to accomplish the described functionality in the context of any modern pacemaker, given the disclosure herein, is within the abilities of one of skill in the art.

Pulse generator 202 generates electrical pacing pulses that are delivered to the RV of the patient's heart via cathode electrode 164 and return anode electrode 162. Pulse generator 202 may include charging circuit 230, switching circuit 232 and an output circuit 234 Charging circuit 230 may include a holding capacitor that may be charged to a pacing pulse amplitude by a multiple of the battery voltage signal of power source 214 under the control of a voltage regulator. The pacing pulse amplitude may be set based on a control signal from control circuit 206. Switching circuit 232 may control when the holding capacitor of charging circuit 230 is coupled to the output circuit 234 for delivering the pacing pulse. For example, switching circuit 232 may include a switch that is activated by a timing signal received from pace timing circuit 242 upon expiration of an AV pacing interval (or LR pacing interval) and kept closed for a programmed pacing pulse duration to enable discharging of the holding capacitor of charging circuit 230. The holding capacitor, previously charged to the pacing pulse voltage amplitude, is discharged across electrodes 162 and 164 through the output capacitor of output circuit 234 for the programmed pacing pulse duration. Examples of pacing circuitry generally disclosed in U.S. Pat. No. 5,507,782 (Kieval, et al.) and in commonly assigned U.S. Pat. No. 8,532,785 (Crutchfield, et al.), both of which patents are incorporated herein by reference in their entirety, may be implemented in pacemaker 14 for charging a pacing capacitor to a predetermined pacing pulse amplitude under the control of control circuit 206 and delivering a pacing pulse.

Memory 210 may include computer-readable instructions that, when executed by control circuit 206, cause control circuit 206 to perform various functions attributed throughout this disclosure to pacemaker 14. The computer-readable instructions may be encoded within memory 210. Memory 210 may include any non-transitory, computer-readable storage media including any volatile, non-volatile, magnetic, optical, or electrical media, such as a random access memory (RAM), read-only memory (ROM), non-volatile RAM (NVRAM), electrically-erasable programmable ROM (EEPROM), flash memory, or other digital media with the sole exception being a transitory propagating signal. Memory 210 may store timing intervals and other data used by control circuit 206 to control the ventricular pacing mode and delivery of pacing pulses by pulse generator 202, e.g., by detecting an atrial systolic event by atrial event detector circuit 240 from the motion sensor signal and setting a pacing escape interval timer included in pace timing circuit 242, according to the techniques disclosed herein.

Power source 214 provides power to each of the other circuits and components of pacemaker 14 as required. Control circuit 206 may execute power control operations to control when various circuits or components are powered to perform various pacemaker functions. Power source 214 may include one or more energy storage devices, such as one or more rechargeable or non-rechargeable batteries. The connections between power source 214 and other pacemaker circuits and components are not shown in FIG. 3 for the sake of clarity.

Telemetry circuit 208 includes a transceiver 209 and antenna 211 for transferring and receiving data via a radio frequency (RF) communication link. Telemetry circuit 208 may be capable of bi-directional communication with external device 20 (FIG. 1) as described above. Motion sensor signals and cardiac electrical signals, and/or data derived therefrom may be transmitted by telemetry circuit 208 to external device 20. Programmable control parameters and algorithms for performing atrial event detection and ventricular pacing control may be received by telemetry circuit 208 and stored in memory 210 for access by control circuit 206.

Figure 4:
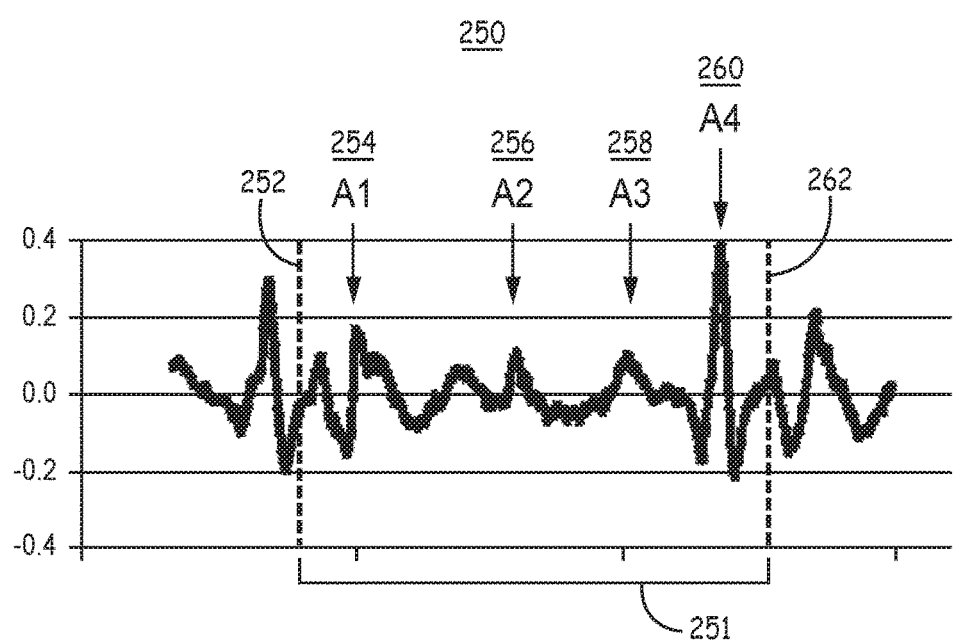
FIG. 4 is an example of a motion sensor signal that may be acquired over a cardiac cycle by a motion sensor included in the ventricular intracardiac pacemaker of FIG. 1.

FIG. 4 is an example of a motion sensor signal 250 that may be acquired by motion sensor 212 over a cardiac cycle. Vertical dashed lines 252 and 262 denote the timing of two consecutive ventricular events (an intrinsic ventricular depolarization or a ventricular pace), marking the respective beginning and end of the ventricular cycle 251. The motion signal includes an A1 event 254, an A2 event 256, an A3 event 258 and an A4 event 260. The A1 event 254 is an acceleration signal (in this example when motion sensor 250 is implemented as an accelerometer) that occurs during ventricular contraction and marks the approximate onset of ventricular mechanical systole. The A1 event is also referred to herein as a "ventricular contraction event." The A2 event 265 is an acceleration signal that occurs during ventricular relaxation and marks the approximate offset or end of ventricular mechanical systole. The A2 event is also referred to herein as the "ventricular relaxation event." The A3 event 258 is an acceleration signal that occurs during passive ventricular filling and marks ventricular mechanical diastole. The A3 event is also referred to herein as the "ventricular passive filling event." Since the A2 event occurs with the end of ventricular systole, it is an indicator of the onset of ventricular diastole. The A3 event occurs during ventricular diastole. As such, the A2 and A3 events may be collectively referred to as ventricular mechanical diastolic events because they are both indicators of the ventricular diastolic period.

The A4 event 260 is an acceleration signal that occurs during atrial contraction and active ventricular filling and marks atrial mechanical systole. The A4 event 260 is also referred to herein as the "atrial systolic event" or merely the "atrial event." The A4 event 260 is the atrial systolic event that is detected from motion sensor signal 250 by atrial event detector circuit 240 for controlling pace timing circuit 242 to trigger ventricular pacing pulse delivery by starting an AV pacing interval in response to detecting the A4 event 260 when pacemaker 14 is operating in an atrial tracking ventricular pacing mode. As described below, control circuit 206 may be configured to detect one or more of the A1, A2, and A3 events from motion sensor signal 250, for at least some ventricular cardiac cycles, for use in positively detecting the A4 event 260 and setting atrial event detection control parameters. The A1, A2 and/or A3 events may be detected and characterized to avoid false detection of A4 events and promote reliable A4 event detection for proper timing of atrial-synchronized ventricular pacing pulses.

Figure 5:
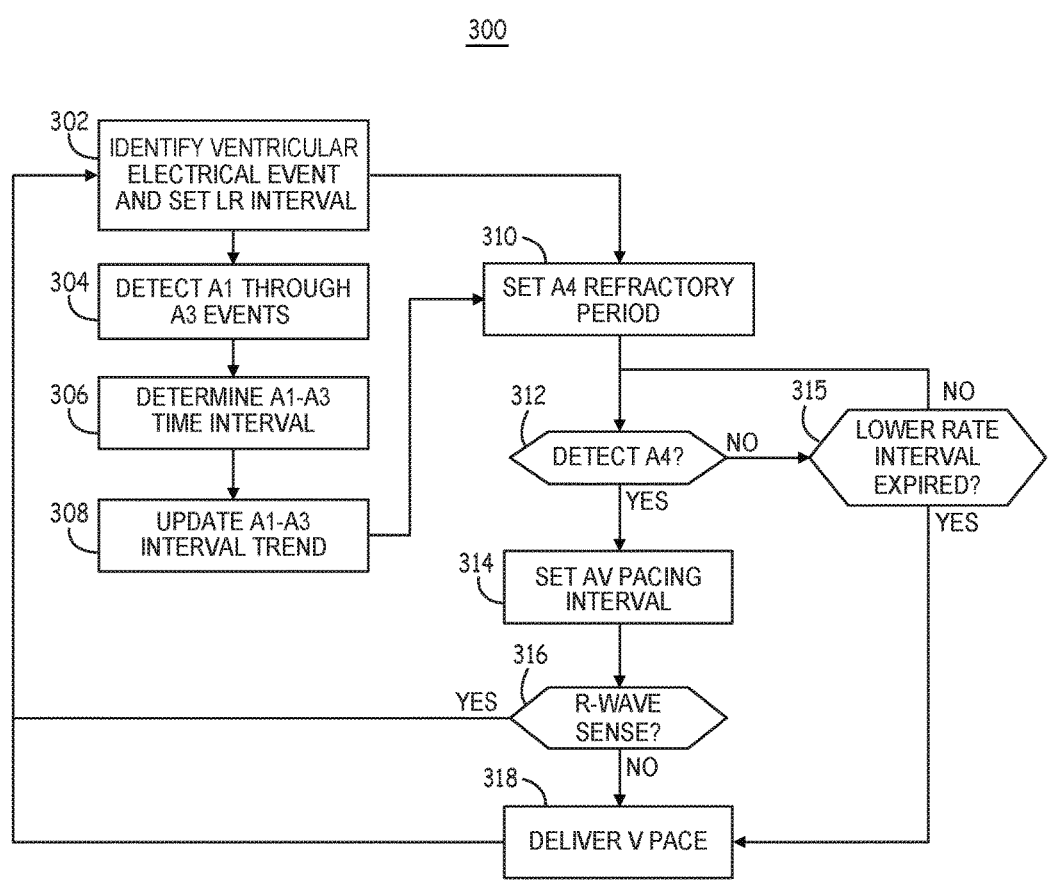
FIG. 5 is a flow chart of one method performed by an intracardiac ventricular pacemaker for detecting an atrial systolic event from a motion sensor signal and controlling ventricular pacing.

FIG. 5 is a flow chart 300 of one method performed by pacemaker 14 for detecting the A4 event and controlling ventricular pacing during an atrial tracking pacing mode. At block 302, control circuit 206 identifies a ventricular event. The ventricular event may be an R-wave sensed event signal received from sensing circuit 204 or a ventricular pacing pulse delivered by pulse generator 202. Since the ventricular A1, A2 and A3 events may have different characteristics during an intrinsic ventricular rhythm than during a ventricular paced rhythm, the methods described herein for determining amplitudes, time intervals or other characteristics of the A1, A2 and A3 events for use in setting A4 detection control parameters or confirming A4 event detection may be determined for both an intrinsic ventricular rhythm and a ventricular paced rhythm.

For example, as described in conjunction with the flow charts and timing diagrams presented herein, various time intervals, sensing windows, atrial refractory period, and atrial event detection threshold amplitude may be set based on characterizations of one or more of the A1, A2 and A3 events. One set of A4 detection control parameters and characteristics of the A1, A2 and A3 events may be determined and stored for use during episodes of ventricular sensing (ventricular intrinsic rhythm), and another set of A4 detection control parameters and characteristics of the A1, A2 and A3 events may be determined and stored for use during episodes of ventricular pacing.

During ventricular sensing, control circuit 206 may be configured to discriminate a normal sinus R-wave from a premature ventricular contraction (PVC) so that ventricular events identified at block 302 for use in starting a search for the A1 through A4 events from the motion sensor signal do not include PVCs. When a ventricular event, sensed or paced, is identified at block 302 that is not a PVC, pace timing circuit 242 may set an escape interval timer to a ventricular LR pacing interval. If the LR pacing interval expires (as described below in conjunction with block 315), a ventricular pacing pulse may be delivered, asynchronous to atrial activity, in order to maintain some minimum, base ventricular rate.

At block 304, atrial event detector 240 detects the A1 through A3 motion signals. Briefly, atrial event detector 240 may compare the motion sensor signal to one or more pre-determined detection threshold amplitudes during one or more time windows set inresponse to identifying the ventricular event at block 302 for detecting the A1 through A3 events. In some examples, the A4 event may also be detected at block 304 to increase confidence in the positive identification of each of the four motion sensor signals A1 through A4 in a given cardiac cycle. In this example, the A1 through A3 events, and optionally A4, may be detected on a beat-by-beat basis.

After the A1 through A3 events are detected, the A1-A3 time interval is determined at block 304 as the time interval from the A1 event detection to the A3 event detection. The A1-A3 time interval may be used to update an A1-A3 interval trend at block 308. For example, a running average A1-A3 time interval may be updated at block 308 using the most recent N A1-A3 time interval measurements, e.g., the most recent three to twelve A1-A3 time intervals.

The A1-A3 time interval is used to set a post-ventricular atrial refractory period at block 310. This atrial refractory period is also referred to herein as an "A4 refractory period" because A4 event detection may be inhibited or ignored during the atrial refractory period in some examples. When a ventricular electrical event is identified at block 302, atrial event detector 240 may start the atrial refractory period at block 310. The atrial refractory period may be set based on the A1-A3 time interval, e.g., to a percentage longer than or a fixed interval longer than the A1-A3 time interval. For example, the atrial refractory period may be set to be 50 to 150 ms longer than the A1-A3 time interval, though shorter or longer fixed intervals may be added to the A1-A3 time interval for setting the atrial refractory period. The fixed time interval used to set the atrial refractory period may vary depending on heart rate in some examples.

During the atrial refractory period, any motion sensor events that are detected, or cross a detection threshold amplitude, are ignored for the purposes of triggering a ventricular pacing pulse and starting an AV pacing interval. Ventricular mechanical events A1 through A3 may be detected during the atrial refractory period, as indicated at block 304, to determine the A1-A3 time interval and update the A1-A3 interval trend (blocks 306 and 308), either periodically or on a beat-by-beat basis.

At block 312, atrial event detector circuit 240 monitors the motion sensor signal to detect the A4 event after the expiration of the atrial refractory period. If the A4 event is not detected before the LR pacing interval expires (block 315), a ventricular pacing pulse is delivered at block 316 to ensure a minimum ventricular rate, e.g., at least 40 to 60 beats per minute. Furthermore, it is to be understood that if an intrinsic R-wave is sensed before an A4 event is detected, the process of FIG. 5 may return to block 302 where the sensed R-wave is identified as a ventricular electrical event and control circuit 206 restarts the process of detecting the A4 event on the next ventricular cycle.

If the A4 event is detected before the LR pacing interval expires, control circuit 206 sets the AV pacing interval at block 314 in response to detecting the A4 event. If an intrinsic R-wave is not sensed from the cardiac electrical signal by sensing circuit 204 during the AV pacing interval, "no" branch of block 316, a ventricular pacing pulse is delivered by pulse generator 202 at block 318 upon expiration of the AV pacing interval. The ventricular pacing pulse, if delivered, and otherwise the sensed R-wave, is identified as the next ventricular event at block 302 and the process repeats.

In this way, the A1 through A3 events may be detected from the motion sensor signal on a beat-by-beat (or less frequent) basis for updating the A1-A3 time interval trend used to set the atrial refractory period to provide a high likelihood of positively detecting the A4 event and properly timing a ventricular pacing pulse in synchrony with the atrial event. Other motion sensor signal events A1 through A3 are unlikely to be falsely detected as the A4 event by applying the atrial refractory period set based on the A1-A3 timing.

In some examples, rather than determining an A1-A3 time interval, a time interval to the A2 event may be determined so that the atrial refractory period is set based on the A1-A2 time interval to extend through at least the A2 event and expire before the A3 event. In this example, an A4 detection threshold amplitude may be set higher than an expected A3 event amplitude to allow detection of the A4 event earlier in the ventricular cycle, for example as the atrial rate is increasing. In other cases, the time interval from the identified ventricular electrical event to the A1, A2 or A3 event may be determined and used in setting the atrial refractory period.

In some examples, the process of blocks 304 through 308 is performed periodically rather than on a beat-by-beat basis. For example detection of A1-A3 events during the atrial refractory period may occur on every third cardiac cycle, every eighth cardiac cycle, once per minute, or other predetermined schedule for updating the A1-A3 time interval (or other ventricular event time interval as discussed above) used for setting the atrial refractory period at block 310. In some cases, the heart rate, paced or intrinsic, may be monitored and the A1-A3 events may be detected for updating the A1-A3 interval trend when the heart rate changes by more than a predetermined amount. For example, ventricular event intervals between consecutive ventricular events may be determined upon identifying ventricular events at block 302. The ventricular event intervals may be RR intervals between consecutively sensed intrinsic R-waves or VV intervals between consecutively delivered ventricular pacing pulses and may include RV intervals between a sensed intrinsic R-wave and a consecutively delivered pacing pulse and VR intervals between a delivered pacing pulse and a consecutively sensed R-wave. Both the intrinsic heart rate and the paced rate may change, e.g., when pacemaker 14 is a rate responsive pacemaker. If the ventricular event interval changes or a trend in the ventricular event interval changes by more than a predetermined amount, the control circuit may perform blocks 304 through 308 to update the A1-A3 interval trend used for setting the atrial refractory period.

In other examples, if the A4 event is not detected at block 312 after the atrial refractory period and before the next ventricular event (intrinsic or paced) is identified at block 302, the control circuit 206 may perform the process of blocks 304 through 306 for a predetermined number of consecutive or non-consecutive cardiac cycles to update the A1-A3 interval trend used to set the atrial refractory period to restore A4 detection.

Figure 6:
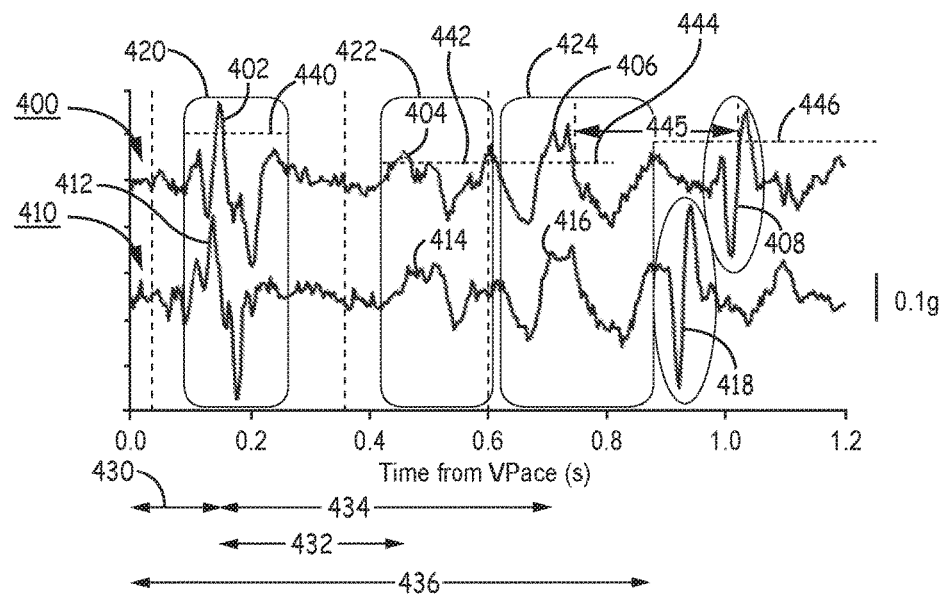
FIG. 6 is an example of a motion sensor signal acquired over two different ventricular cycles.

FIG. 6 is an example of a motion sensor signals 400 and 410 acquired over two different cardiac cycles. A ventricular pacing pulse is delivered at time 0.0 seconds for both cardiac cycles. The top sensor signal 400 is received over one cardiac cycle and the bottom sensor signal 410 is received over a different cardiac cycle. The two signals 400 and 410 are aligned in time at 0.0 seconds, the time of the ventricular pacing pulse delivery.

The A1 events 402 and 412 of the respective motion sensor signals 400 and 410, which occur during ventricular contraction, are observed to be well-aligned in time following the ventricular pacing pulse at time 0.0 seconds. Similarly, the A2 events 404 and 414 (occurring during ventricular relaxation) and the A3 events 406 and 416 (occurring during passive ventricular filling) are well-aligned in time. Since the A1, A2 and A3 events are ventricular events, occurring during ventricular contraction, ventricular relaxation, and passive ventricular filling, respectively, these events are expected to occur at relatively consistent intervals following a ventricular electrical event, the ventricular pacing pulse in this example, and relative to each other. The time relationship of the A1, A2 and A3 events may be different following a ventricular pacing pulse compared to following a sensed intrinsic R-wave, however, during a stable paced or intrinsic ventricular rhythm, the relative timing of A1, A2 and A3 events to each other and the immediately preceding ventricular electrical event is expected to be consistent for a given heart rate.

The A4 events 408 and 418 of the first and second motion sensor signals 400 and 410 respectively are not aligned in time. The A4 event occurs during atrial systole and as such the time interval of the A4 event following the immediately preceding ventricular electrical event (sensed R-wave or ventricular pacing pulse) and the preceding A1 through A3 events may vary between cardiac cycles.

The consistency of the timing of the A1 through A3 events relative to each other and the immediately preceding ventricular electrical event may be used for determining the atrial refractory period and increasing confidence in reliably detecting A4 events 408 and 418. In some examples, an A1 sensing window 420 may be set based on an expected Vpace-A1 time interval. The Vpace-A1 time interval 430 may be measured when the motion sensor signal 400 or 410 crosses an A1 sensing threshold amplitude 440. The A1 sensing window 420 may be adjusted on the next cardiac cycle based on the Vpace-A1 time interval 430 determined on the current cardiac cycle or a running average Vpace-A1 time interval.

An A2 sensing window 422 may be set based on an expected Vpace-A2 time interval (not explicitly shown but understood to be the total time from 0.0 seconds to an A2 event detection) or an A1-A2 time interval 432 (time from A1 detection to time of A2 detection). The A2 event 404 or 414 may be detected at the time of the first positive-going crossing of an A2 sensing threshold amplitude 442 by the motion sensor signal 400 or 410 during the A2 sensing window 422. The A2 sensing window 422 may be adjusted on the next cardiac cycle based on the Vpace-A2 time interval or A1-A2 time interval 432 determined on the current cardiac cycle.

Similarly, an A3 sensing window 424 may be set based on an expected Vpace-A3 time interval (not explicitly labeled but understood to be sum of time intervals 430 and 434), A1-A3 time interval 434, or A2-A3 time interval (not explicitly labeled but understood to be the time interval from the sensed A2 event 404 or 414 to the sensed A3 event 406 or 416). The A3 event 406 or 416 may be detected during the A3 sensing window 424 when the motion sensor signal 400 or 410, respectively, crosses an A3 sensing threshold amplitude 444. The threshold crossing resulting in an A3 event detection may be the first positive going threshold crossing, the last negative going threshold crossing (of a rectified signal) or another fiducial point of the A3 event signal. The A3 sensing window 424 may be adjusted on the next cardiac cycle based on the Vpace-A3 time interval, A1-A3 time interval 434, or the A2-A3 time interval determined during the current cardiac cycle.

Each of the sensing windows 420, 422 and 424 may be set based on a history of time intervals determined from a ventricular pacing pulse or sensed intrinsic R-wave to the respective A1 event 402 or 412, A2 event 404 or 414 and A3 event 406 or 416 or based on a history of time intervals between the detected A1, A2 and A3 events or any combination thereof. For example, the A2 sensing window 422 may be set to start based on time intervals measured between a ventricular pacing pulse or sensed R-wave and the detected A1 event. The end of the A2 sensing window 422 may be set to start based on an A1-A2 time interval 432 or based on an A1-A3 time interval 434. It is recognized that numerous methods may be conceived for setting the A1, A2 and A3 sensing windows 420, 422 and 424, respectively, based on the consistency of the expected time intervals between any combinations of the ventricular electrical event (paced or sensed) and subsequent A1, A2 and A3 events.

Furthermore, it is contemplated that these sensing windows 420, 422 and 424 may be set according to different control parameters, such as different fixed time intervals added to or subtracted from measured event time intervals depending on whether the ventricular electrical event is a paced or sensed event and/or depending on heart rate. The event time intervals that may be measured and used for setting the onset, offset and duration of the sensing windows 420, 422 and 424 may include any one or combination of the Vpace-A1, Vpace-A2, Vpace-A3, Rsense-A1, Rsense-A2, Rsense-A3, A1-A2, A1-A3, and/or A2-A3 time intervals determined during a paced and/or intrinsic rhythm.

The sensing threshold amplitudes 440, 442 and 444 may be set uniquely during each of the respective sensing windows 420, 422 and 424, respectively, or set to a fixed common value for all sensing windows. The sensing threshold amplitudes 440, 442, and 444 may be fixed or decaying thresholds and may be automatically adjusted thresholds set to starting threshold values based on the peak motion sensor signal amplitude detected during each respective window 420, 422 and 424. The motion sensor signals 400 and 410 are shown as raw signals, but the motion sensor signal may be filtered, amplified and rectified by circuitry included in motion sensor 212 to provide control circuit 206 with a rectified signal that is used to detect the A1 through A4 events.

A post-ventricular, atrial refractory period 436 may be set based on the A1-A3 time interval 434 or based on the Vpace-A3 time interval (sum of Vpace-A1 interval 430 and A1-A3 time interval 434). In some examples, the atrial refractory period 436 ends upon the expiration of the A3 sensing window 424. In other examples, the atrial refractory period 436 ends after the expiration of the A3 sensing window 424. The A4 event 408 or 418 may be detected in response to a crossing of an A4 sensing threshold amplitude 446, e.g., the first positive-going crossing or a last negative-going crossing, by the rectified motion sensor signal.

In some examples, the A4 detection is confirmed when the A1, A2 and A3 events have each been detected during the atrial refractory period 436. If any one of the A1, A2 or A3 events was not detected during the atrial refractory period 436, the A4 event detection based on a crossing of threshold 446 may not be confirmed and not used for starting an AV pacing interval. In other examples, at least one of the A1, A2 or A3 events may be required to be detected during a respective sensing window 420, 422, or 424 on a beat-by-beat basis for confirming an A4 detection after the atrial refractory period 436.

The A1, A2 and/or A3 events sensed during the respective A1 sensing window 420, A2 sensing window 422 and A3 sensing window 424 may be used for updating the atrial refractory period 436 as described in conjunction with FIG. 5 on a beat-by-beat or less frequent basis without requiring positive detection of each of A1, A2, and/or A3 for confirming an A4 detection on each beat. Setting the atrial refractory period based on detection and relative timing of the A1 through A3 events enables the atrial refractory period to be set based on the consistent timing of the ventricular motion sensor signal events so that A4 events may be detected with high reliability even when the timing of the A4 event relative to the A1-A3 events and the preceding ventricular electrical event is variable.

In some examples, an A3-A4 event interval 445 is determined and used for adjusting the A4 refractory period 436. For example, the A3 event 406 may be detected by detecting the last, negative-going crossing of an A3 event detection threshold amplitude 444 during the A3 sensing window 424. The A4 event 408 may be detected by the first positive-going crossing of the A4 event detection threshold amplitude 446 after the expiration of the A4 refractory period 436. The A3-A4 event interval 445 is determined as the time from the A3 event detection and the time of the A4 event detection. This A3-A4 event time may be compared to a previous A3-A4 event time, e.g., compared to one or more preceding A3-A4 event times which may be determined during the respective one or more preceding cardiac cycles or to a running average A3-A4 event time determined from two to five or other predetermined number of previously determined A3-A4 event times. If a change in the A3-A4 event time interval compared to one or more preceding A3-A4 event times is detected, the A4 refractory period 436 may be adjusted. As the A3-A4 event time is detected to shorten or increase, the control circuit 206 may decrease or lengthen the A4 refractory period, respectively, to account for changes in the time interval between the ventricular diastolic event and the atrial systolic event as the atrial rate changes.

Figure 7:
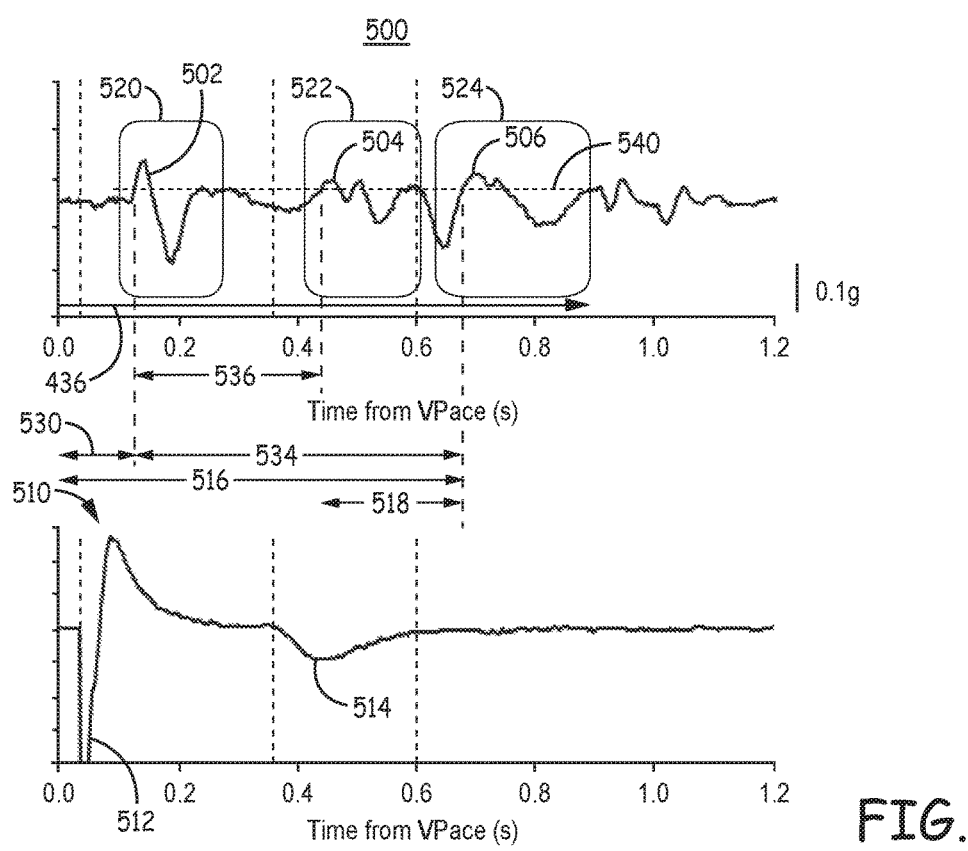
FIG. 7 is an averaged motion sensor signal.

FIG. 7 is an averaged motion sensor signal 500 that may be determined by control circuit 206 by averaging the motion sensor signal obtained over multiple cardiac cycles, e.g., signals 400 and 410 of FIG. 6. The averaged motion sensor signal 500 may represent the average of 3 to 20 or other predetermined number of cardiac cycles. The raw motion sensor signal or a filtered, amplified and/or rectified motion sensor signal may be buffered beginning from a ventricular electrical event, pacing pulse or sensed R-wave, at time 0.0 seconds until the next ventricular electrical event. The buffered motion sensor signal obtained over one cardiac cycle may be averaged with the buffered motion sensor signals obtained over a predetermined number of other cardiac cycles to produce averaged motion sensor signal 500.

A ventricular electrical signal 510 is shown aligned in time with averaged motion sensor signal 500. Ventricular electrical signal 510 may be passed from sensing circuit 204 to control module 206 and includes an R-wave 512, which may be an evoked or intrinsic R-wave, and a T-wave 514. R-wave 512 is followed by the ventricular contraction A1 event 502. The ventricular relaxation A2 event 504 occurs during T-wave 514. The passive ventricular filling A3 event 506 occurs after T-wave 514.

Since the A1, A2 and A3 events are ventricular mechanical events, they occur at consistent time intervals relative to each other and relative to ventricular electrical events (R-wave 512 and T-wave 514). As a result, the signal-to-noise ratio of the A1 signal 502, A2 signal 504 and A3 signal 506 is improved in the averaged motion sensor signal 500 compared to the single-cycle motion sensor signals 400 and 410 of FIG. 6. The averaged A1 event 502, A2 event 504 and A3 event 506 have an improved signal-to-noise ratio compared to the A1, A2 and A3 events observed in the motion sensor signal 400 or 410 of a single cardiac cycle as shown in FIG. 6, making A1, A2, and A3 event detection from the averaged motion signal 500 more reliable.

A single event detection threshold amplitude 540 may be defined such that the a crossing of the threshold 540 by the averaged, rectified motion sensor signal 500 within the A1 sensing window 520, A2 sensing window 522 and A3 sensing window 524 is detected as the respective A1 event 502, A2 event 504, and A3 event 506. The threshold crossing may be a first, positive-going crossing or a last, negative-going crossing in various examples. Alternatively, unique detection threshold amplitudes may be defined for each sensing window 520, 522 and 524 for detecting the respective A1, A2 and A3 events. The sensing windows 520, 522 and 524 may be initially set according to expected A1, A2 and A3 event timing following the ventricular pacing pulse or R-wave 512 and may be adjusted according to the actual detection time of each respective A1 event 502, A2 event 504, and A3 event 506 based on a threshold crossing. The sensing windows 520, 522 and 524 may be set based on ventricular pacing rate or atrial event rate, e.g., based on A4-A4 event intervals. The sensing windows 520, 522 and 524 may also be set differently following a ventricular pacing pulse than following an intrinsic R-wave sensed event since the timing of the A4, A2 and A3 events and T-wave 514 may be altered during ventricular pacing compared to during an intrinsic ventricular rhythm.

The atrial systolic A4 event timing, which is independent of the ventricular electrical event timing, may be more variable from one cardiac cycle to the next with respect to the ventricular electrical and mechanical events, e.g., as shown by the relative timing of the A4 events 408 and 418 of signals 400 and 410 (FIG. 6). As a result, the A4 signal is largely attenuated in the averaged motion signal 500 in FIG. 7. The improved signal-to-noise ratio of the A1 through A3 events and attenuation of the A4 event in the averaged motion signal 500 enables control circuit 206 to reliably detect the signal averaged A1 event 502, A2 event 504 and A3 event 506 for determining one or more ventricular event time intervals for use in setting A1, A2 and A3 detection windows 420, 422, and 424, respectively, setting detection threshold amplitudes for detecting the A1, A2, A3 and/or A4 events, and/or setting atrial refractory period 436 used on a beat-by-beat basis for A4 event detection as shown in FIG. 6.

For example, a ventricular R-wave or pacing pulse to A1 time interval 530, an A1-A3 time interval 534, A1-A2 time interval 536, a ventricular R-wave or pacing pulse to A3 time interval 516, and/or a T-wave to A3 time interval 518 may be determined by control circuit 206 from the averaged motion signal 500 and the cardiac electrical signal 510. The atrial refractory period 436 is started upon delivering a ventricular pacing pulse or sensing an intrinsic R-wave. The atrial refractory period 436 may be set to expire after a predetermined time interval, e.g., 30 to 100 ms, after the A3 time interval 516. For instance, if time interval 516 is 700 ms, the atrial refractory period 436 may be set to expire 750 ms after the ventricular pacing pulse or sensed R-wave that started the atrial refractory period. Instead of using a time interval ending with the A3 event detection, a time interval ending with the A2 event detection may be determined and used in controlling the duration of the atrial refractory period 436. As described above, the A2 event, which occurs during T-wave 514, is an indicator of the end of ventricular mechanical systole and the onset of ventricular mechanical diastole. The A3 event occurs during ventricular mechanical diastole, during the passive ventricular filling phase. As such the timing of the A2 event 504 or the timing of the A3 event 506 relative to another ventricular electrical event (ventricular pacing pulse, R-wave 512, or T-wave 514) may be used for controlling the duration and expiration time of atrial refractory period 436. In other words, the timing of a ventricular mechanical diastolic event, A2 event 504 or A3 event 506, may be determined and used to set the atrial refractory period 436 that is applied on a beat-by-beat basis for detecting A4 events.

The T-wave 514 may be sensed by sensing circuit 206 on a beat-by-beat basis by control circuit 206 or by sensing circuit 204 from cardiac electrical signal 510. The T-wave 514 may be sensed at a maximum peak amplitude of a rectified cardiac electrical signal or a maximum absolute peak amplitude in a non-rectified cardiac signal received by control circuit 206 from sensing circuit 204. Alternatively, T-wave 514 may be sensed by sensing circuit 204 in response to the cardiac electrical signal crossing a T-wave sensing threshold amplitude after the ventricular pacing pulse or R-wave sensed event signal. In some cases, a T-wave sensing window may be applied after the R-wave sensed event signal or a delivered pacing pulse to facilitate T-wave sensing.

The T-wave 514 may be sensed during the atrial refractory period 436. Control circuit 206 may terminate the atrial refractory period 436 at a predetermined time interval after sensing T-wave 514. For instance if the T-wave to A3 time interval 518 is determined to be 150 ms from the averaged motion signal 500, control circuit 206 may terminate the atrial refractory period 436 at 180 ms after sensing the T-wave to promote reliable sensing of the A4 event.

Atrial event detector circuit 240 may be a processor-based circuit that determines the averaged motion sensor signal 500 over multiple cardiac cycles, detects A1, A2 and A3 events 502, 504, and 506 from the averaged motion sensor signal 500, and sets the atrial refractory period 436 based on the timing of at least one ventricular mechanical diastolic event, e.g., the A3 event 506, detected from the average motion sensor signal 500. In other examples, the A2 event is used as a ventricular diastolic mechanical event for marking the approximate timing of the onset of ventricular diastole. The A4 event, e.g., event 408 or 418 (FIG. 6) may be detected on a beat-by-beat basis from the non-averaged motion sensor signal after the atrial refractory period 436 expires.

Figure 8:
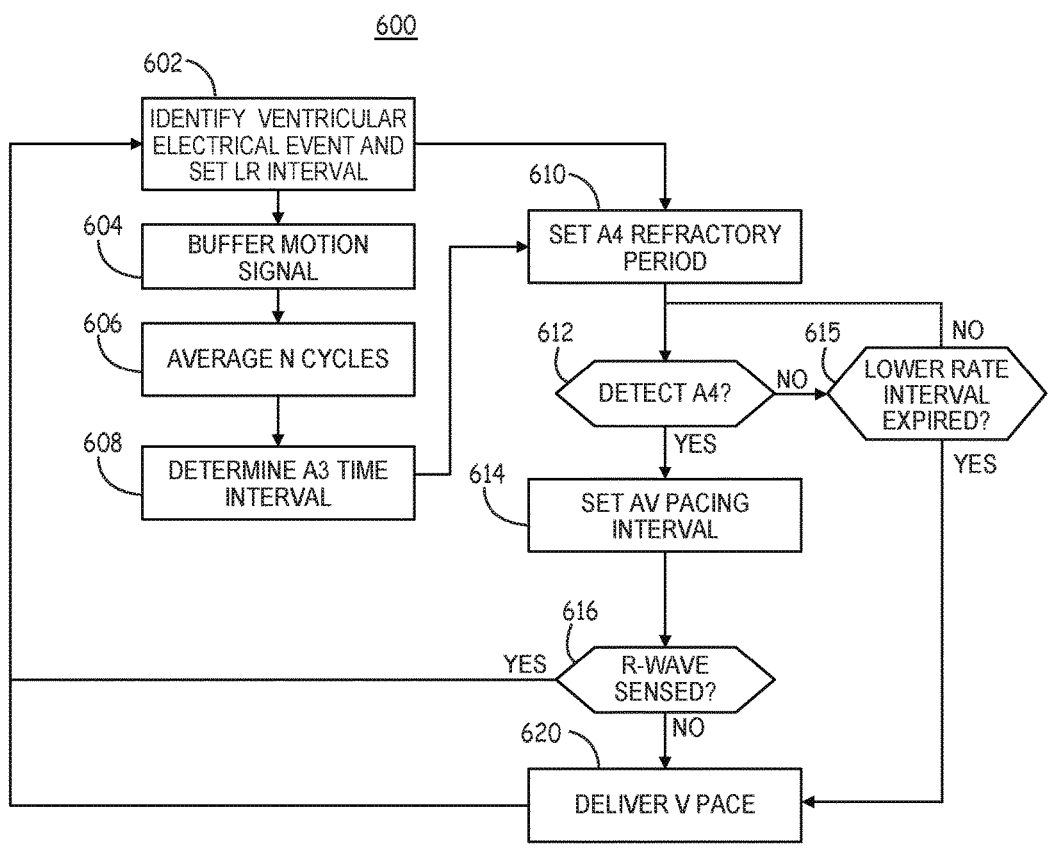
FIG. 8 is a flow chart of a method performed by an intracardiac ventricular pacemaker for detecting atrial events and controlling atrial-synchronized ventricular pacing according to another example.

FIG. 8 is a flow chart 600 of a method performed by pacemaker 14 for detecting atrial events and controlling atrial-synchronized ventricular pacing during an atrial tracking pacing mode according to one example. At block 602, a ventricular electrical event is identified, which may be a sensed intrinsic R-wave or delivered ventricular pacing pulse. A LR pacing interval may be set at block 602 upon identifying the ventricular electrical event, as described in conjunction with FIG. 5, in order to maintain a minimum, base ventricular rate in the absence of A4 event detections.

At block 604, the motion sensor signal is buffered over the cardiac cycle, e.g., until the next ventricular electrical event is identified. At block 606, the buffered motion signal is averaged with buffered motion sensor signals acquired over a predetermined number of cardiac cycles to obtain an averaged motion signal with improved A1, A2 and A3 signal-to-noise ratio and attenuated A4 signal compared to the non-averaged motion sensor signal.

At block 608 the A1-A3 time interval or a ventricular electrical event to A3 time interval is determined from the averaged motion sensor signal by detecting the signal averaged A1, A2 and A3 events as described above in conjunction with FIG. 7. The A3 time interval is used to set the atrial refractory period at block 610 by atrial event detector circuit 240. As described above, the atrial refractory period may be set a predetermined percentage or fixed time interval longer than the A1-A3 time interval or a ventricular electrical event to A3 time interval or set to expire upon expiration of an A3 sensing window that is defined based on relative timing of the A1, A2, and A3 events. In other examples, an A2 time interval is determined at block 608 for use in setting the A4 refractory period. The A2 and A3 events are ventricular mechanical diastolic event markers that may be used for controlling the timing of the expiration of the A4 refractory period to occur near the start or during the ventricular passive filling phase, before the active ventricular filling phase associated with atrial systole.

The atrial refractory period is started at block 610 upon identifying the ventricular electrical event at block 602. In some examples, signal averaging and determination of the A3 time interval (or A2 time interval) for setting the atrial refractory period may occur on a beat-by-beat basis using an averaged motion signal. In other examples, the A3 time interval is determined periodically or in response to a change in the atrial rate, e.g., determined from A4-A4 intervals, or a change between a sensed and paced ventricular rhythm. The most recently updated A3 time interval (or A2 time interval) determined from the averaged motion sensor signal may be used to set the atrial refractory period at block 610. The expiration of the atrial refractory period may be set on the fly during an already started atrial refractory period based on the A3 time interval determined during the current ventricular cycle. In other examples, the A3 time interval determined on a preceding ventricular cycle is used to set the atrial refractory period for the current ventricular cycle so that the atrial refractory period ends during or after an expected time of the A3 event, or in some cases prior to an expected A3 event but after an expected A2 event.

In other examples, the duration of the atrial refractory period may be controlled on a beat-by-beat basis by starting the atrial refractory period upon the identified ventricular event, sensing the T-wave during the atrial refractory period, and terminating the atrial refractory period a predetermined time interval after the sensed T-wave, where the predetermined time interval is based on the T-wave to A3 time interval 518 determined from the averaged motion signal 500 (FIG. 7).

If an A4 event is detected from the non-averaged motion sensor signal at block 612, after the atrial refractory period expires, an AV pacing interval is set at block 614. The A4 event may be detected based on an A4 detection threshold amplitude crossing by the raw motion sensor signal or by the rectified signal. The pace timing circuit 242 sets an AV pacing interval at block 614 in response to the detected A4 signal. If an intrinsic R-wave is not sensed before expiration of the AV pacing interval, as determined at block 616, the scheduled ventricular pacing pulse is delivered at block 620. In some cases, the A4 event may not be detected before a lower rate pacing interval expires at block 615. An atrial-asynchronous ventricular pacing pulse may be delivered at block 620 if the lower rate pacing interval expires before an A4 event is detected to maintain a programmed minimum ventricular base rate, causing the process to return to block 602 where the ventricular pacing pulse is identified as the next ventricular electrical event.

Figure 9:
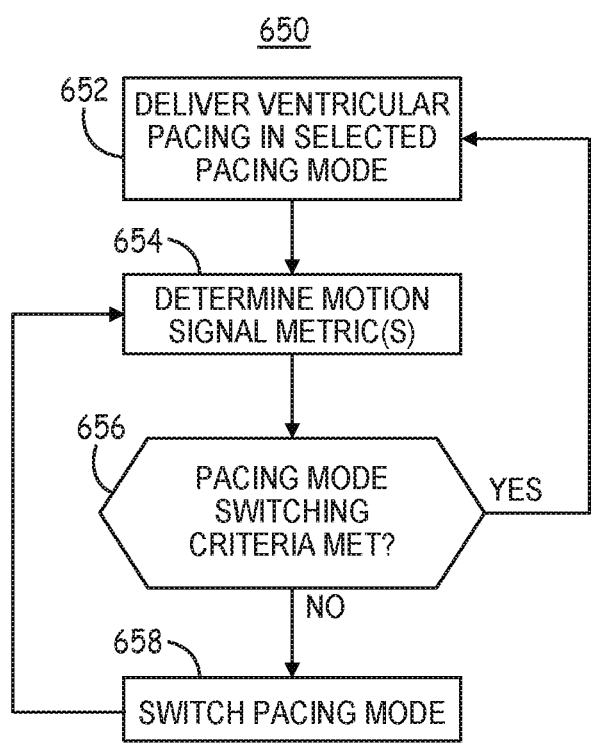
FIG. 9 is a flow chart of a method for controlling ventricular pacing mode by an intracardiac ventricular pacemaker according to one example.

FIG. 9 is a flow chart 650 of a method for controlling ventricular pacing mode by pacemaker 14 according to one example. Control circuit 206 is configured to control pacemaker 14 to operate in a first pacing mode, either an atrial-tracking pacing mode or a non-atrial tracking pacing mode for controlling ventricular pacing pulses and to determine when to switch to a second pacing mode, the other one of the atrial-tracking pacing mode or the non-atrial tracking pacing mode, based on an analysis of the motion sensor signal.

As shown in FIG. 9, ventricular pacing pulses are delivered according to the selected pacing mode at block 652. For example, the pacemaker 14 may be operating in an atrial-tracking VDD pacing mode during which ventricular pacing pulses are scheduled at an AV pacing interval in response to detecting an A4 event. In the absence of a detected A4 event, a ventricular pacing pulse is delivered at a VDD lower rate (LR) interval when an intrinsic R-wave is not detected before expiration of the LR interval to prevent ventricular asystole. At other times, the pacemaker 14 may be operating in a non-atrial tracking VVIR or VDIR pacing mode during which pacing pulses are scheduled at a ventricular LR pacing interval, which may be a permanent VVIR or VDIR LR interval corresponding to a base pacing rate or a temporary LR interval set based on a patient physical activity metric determined from the motion sensor signal (or other sensor signal correlated to patient metabolic demand).

During operation the selected ventricular pacing mode, the control circuit 206 is configured to determine one or more motion signal metrics from the motion signal at block 654. The one or more motion signal metrics are compared to first pacing mode switching criteria at block 656. If the first pacing mode switching criteria are met, the control circuit switches from the current, first pacing mode, either an atrial tracking pacing mode or a non-atrial tracking pacing mode, to a second pacing mode (block 658). The second pacing mode is the other one of the atrial tracking pacing mode or the non-atrial tracking pacing mode depending on which pacing mode the control circuit 206 is switching from.

During the second pacing mode, the control circuit 206 determines one or more motion signal metrics at block 654, which may be the same motion signal metric(s) or different motion signal metric(s) that were determined during the first pacing mode. Control circuit 206 determines if second pacing mode switching criteria are met by the motion signal metric(s) during the second pacing mode and switches back to the first pacing mode in response to the second pacing mode switching criteria being met.

Among the motion signal metrics that may be determined at block 654 are metrics that are correlated to patient physical activity and/or correlated to loss of reliable A4 event detection. Motion signal metrics correlated to patient physical activity may be a patient activity metric correlated to patient metabolic demand such as an activity count or a sensor indicated pacing rate determined from the patient activity metric. A patient posture may be determined from the motion signal as an indirect indicator of patient activity, e.g., by detecting a non-upright posture as a resting or inactive posture and detecting an upright posture as a non-resting or active posture. Patient posture may also be determined as a motion signal metric that is correlated to loss of reliable A4 event detection since the patient posture may influence the A4 signal strength and reliability of A4 event detection. For example, a particular patient posture, for instance a left side-lying posture or other identified posture, may be determined to confound A4 event detection in an individual patient and be criteria for pacing mode switching.

A motion signal metric that may be determined at block 654 that is correlated to loss of reliable A4 event detection may be a count of ventricular cycles that occur without a detected A4 event. Another motion signal metric that may be correlated to a loss of reliable A4 event detection may be the A3 -A4 time interval. Shortening of the A3 -A4 time interval, e.g., interval 445 in FIG. 6, or another ventricular event to A4 time interval, may indicate an increasing atrial rate that may lead to fusion of the A3 and A4 events and/or be associated with increased patient physical activity, both of which may confound A4 event detections.

A motion signal metric that may be determined at block 654 that is correlated to both patient physical activity and loss of reliable A4 event detection may be determined by processing motion signal sample points acquired over a predetermined time segment of the motion signal. For example, the average amplitude of all sample points during the predetermined time segment, a summation of the sample point amplitudes during predetermined time segment, the mean frequency during the time segment, mean slope, or other metric of the motion signal energy or entropy during the entirety of the predetermined time segment may indicate an increase in patient physical, non-cardiac motion, signal noise and/or a potential decrease in the reliability of A4 event detection due to increased motion signal peaks present in the motion signal. The time segment for determining the motion signal metric may be one cardiac cycle or portion thereof or may be independent of cardiac cycle timing, e.g., any 500 ms, 1 second, 2 second or other predetermined time segment or multiple predetermined time segments of the motion sensor signal.

Accordingly, the one or more motion signal metrics determined at block 654 may include direct or indirect metrics of non-cardiac, patient physical motion and/or A4 event detection reliability. The motion signal metrics determined from the motion sensor signal included in pacemaker 14 may include metrics of patient physical activity; patient body posture; A4 event detection counts; cardiac mechanical event (A1, A2, A3 , and/or A4) time intervals, amplitudes and/or other features; and motion signal metrics determined by processing the motion signal sample points over a predetermined time segment to obtain a metric correlated to the motion signal energy and/or entropy over the entirety of the time segment.

Figure 10A:
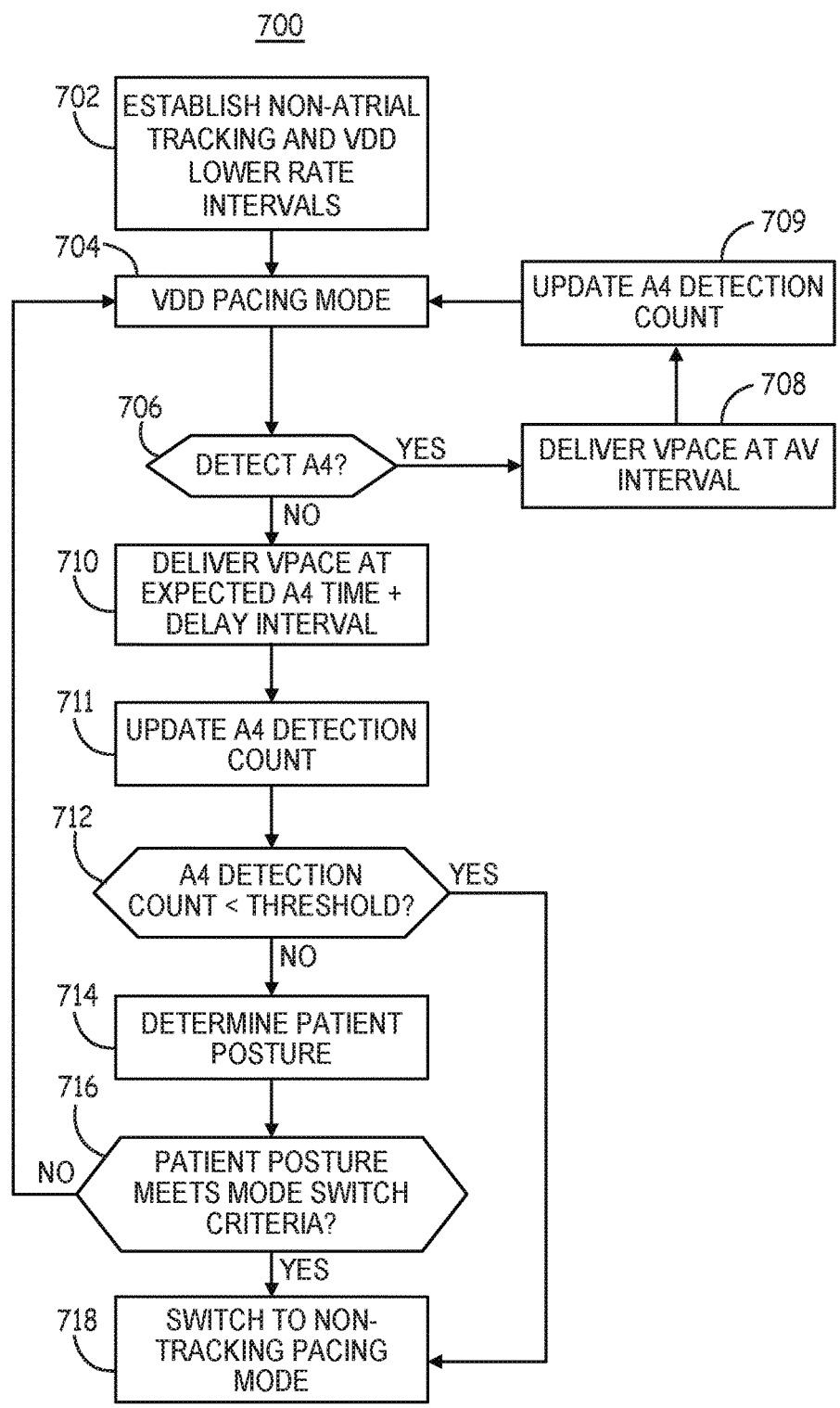
FIG. 10A is a flow chart of a method performed by an intracardiac ventricular pacemaker for switching from an atrial tracking pacing mode to a non-atrial tracking pacing mode according to one example.

FIG. 10A is a flow chart 700 of a method performed by pacemaker 14 for switching from the atrial tracking pacing mode to a non-atrial tracking pacing mode based on motion signal metrics according to one example. The methods depicted by the flow charts of FIG. 5 and FIG. 8 generally represent an atrial tracking ventricular pacing mode, such as a VDD pacing mode, in which ventricular pacing pulses are delivered based on dual chamber (atrial and ventricular) sensing of cardiac events (e.g., at least ventricular R-waves and atrial A4 events) by RV pacemaker 14 and providing a dual pacing response of both triggered and inhibited pacing pulses. Ventricular pacing pulses are triggered in response to detecting an A4 event from the motion sensor signal. Ventricular pacing pulses are inhibited in response to sensing a ventricular R-wave.

The LR pacing interval set at blocks 302 and 602 of FIG. 5 and FIG. 8, respectively, may be a VDD LR pacing interval that provides ventricular pacing at a minimum or base ventricular rate in the absence of a sensed A4 event and a sensed R-wave during the LR pacing interval. The VDD LR pacing interval may be set to provide a base pacing rate of 40 beats per minute. As long as the A4 events are being sensed, ventricular pacing is provided in synchrony with atrial systolic events at the atrial rate, which may be paced by atrial pacemaker 12 or an intrinsic atrial rate. As the patient's heart rate changes due to changes in patient physical activity or metabolic demand, the ventricular paced rate will track the changes in the rate of the A4 events.

In some instances, however, the A4 events may be undersensed. For example, the A4 signal may have a low signal strength at times and go undetected. In some patients, postural changes, changes between a paced and intrinsic atrial rhythm or other factors may affect the A4 event amplitude. The patient may have a normal sinus rhythm, but the atrial systolic events are not being detected by pacemaker 14. In this case, atrial tracking of the ventricular pacing pulses is desired but the atrial rate is unknown. As such, switching to a non-atrial tracking pacing mode may be warranted. In other instances, A4 events may be under-detected due to an atrial tachyarrhythmia. During atrial fibrillation, the A4 signal may become too small to be detected. In this case non-atrial tracking ventricular pacing is appropriate to avoid pacemaker-mediated tachycardia.

In both of these situations of A4 events being under-detected, during normal sinus rhythm or during an atrial tachyarrhythmia, ventricular pacing at a rate that adequately supports the patient's physical activity is needed in patients with AV block. The method of flow chart 700 provides one technique for switching the ventricular pacing mode from an atrial tracking VDD pacing mode to a non-atrial tracking pacing mode based on mode switching criteria being satisfied. The mode switching criteria are defined to promote switching to non-atrial tracking ventricular pacing when A4 events are being under-detected and ventricular rate support is needed. The mode switching criteria may be defined to preferentially provide atrial synchronized ventricular pacing in the VDD pacing mode when A4 events are being detected or when A4 events are not being detected but ventricular pacing at the programmed VDD lower rate is adequate for supporting the patient's physical activity level, e.g., a resting state.

At block 702 of FIG. 10A, a first LR interval is established for the atrial tracking pacing mode, e.g., a VDD pacing mode, and a second LR interval is established for the non-atrial tracking mode, e.g., a VVIR or VDIR pacing mode. As described below in conjunction with FIGS. 11 and 12, the non-atrial tracking pacing mode may be a VVIR pacing mode in which sensing of A4 events is disabled most of the time to conserve pacemaker battery longevity but may be temporarily re-enabled to check if pacing mode switching criteria relating to A4 event detection are satisfied. In other examples, as described in conjunction with FIG. 13, the non-atrial tracking pacing mode may be a VDIR pacing mode which still detects and monitors for A4 events, which may be on a beat-by-beat basis, but doesn't trigger ventricular pacing pulses in response to detecting an A4 event.

The atrial tracking LR pacing interval and the non-atrial tracking LR pacing interval may be established by control circuit 206 at block 702 according to programmed respective atrial-tracking and non-atrial tracking lower rates stored in memory 210. The LR intervals established at block 702 are sometimes referred to as the "permanent" LR intervals since they correspond to a programmed base or minimum pacing rate. The permanent LR interval may be adjusted to a temporary LR interval under some circumstances. For example, during rate responsive VVIR pacing, the permanent VVIR LR interval may be shortened to a temporary LR interval to meet the patient's physical activity demand. As described below, when pacing mode switching criteria are satisfied, the pacemaker 14 switches from the atrial tracking pacing mode (e.g., as represented by FIG. 5 or FIG. 8) to the non-atrial tracking pacing mode to provide ventricular pacing in a rate responsive pacing mode in order to maintain an appropriate ventricular rate to meet the patient's physical activity level.

The non-atrial tracking LR interval may be set to provide pacing at a different lower rate than the atrial tracking LR interval. For example, the atrial tracking LR interval may be established at block 702 to provide VDD pacing at a base pacing rate of 40 pulses per minute. The non-atrial tracking LR interval may be established at block 702 to provide a base pacing rate of 60 pulses per minute. By providing a longer LR pacing interval during the atrial tracking pacing mode, greater time is allowed for detecting A4 events during each ventricular pacing cycle to promote atrial-synchronized ventricular pacing. The base pacing rate of 40 pulses per minute corresponding to the atrial tracking LR interval provides pacing when the A4 event is intermittently under-detected. Rate smoothing may be provided to avoid sudden ventricular rate changes. When the A4 events are being consistently under-detected for multiple ventricular cycles, switching to the non-atrial tracking pacing mode with a higher base pacing rate of 60 pulses per minute provides adequate rate support for the patient during a resting or relatively low physical activity state.

At block 704, pacemaker 14 operates in a VDD pacing mode. In some patients, the atrial rate may be intrinsically controlled by the sinus node and increase and decrease physiologically in response to changes in patient physical activity. In other examples, the atrial rate may be paced by atrial pacemaker 12, which may be a rate responsive pacemaker including a patient activity sensor used for determining a sensor indicated pacing rate that matches the metabolic need of the patient. In either case, ventricular pacemaker 14 is configured to detect the intrinsic or paced A4 systolic events on a beat-by-beat basis. In response to detecting the A4 event at block 706, an AV pacing interval is started and upon its expiration a ventricular pacing pulse is delivered at block 708. It is recognized that if an intrinsic R-wave is sensed before the AV pacing interval expires, the ventricular pacing pulse is withheld, e.g., as described above in conjunction with FIG. 8.

At block 709, a count of A4 event detections is updated. For example, an X of Y counter included in control circuit 206 for counting the number of A4 event detections out of a total predetermined number of Y ventricular cycles may be updated. In other examples, a counter may be used to track the number of consecutive ventricular cycles that occur without detecting an A4 event. In this case, the counter may be reset to zero at block 709 in response to the detected A4 event at block 706. A counter for tracking A4 event detections (or ventricular cycles without A4 detections), which may or may not be required to be on consecutive ventricular cycles, may be determined as one motion signal metric used for controlling pacing mode switching.

If an A4 event is not detected before a VDD LR interval expires, the ventricular pacing pulse is delivered at block 710. The VDD LR interval may be adjusted according to a rate smoothing algorithm to avoid a sudden change in ventricular rate. The ventricular pacing pulse delivered at block 710 may be delivered at a pacing interval that is between the expected A4 event time and the VDD LR pacing interval established at block 702 corresponding to a minimum base rate. For instance, the VDD LR interval may be adjusted at block 710 from a VDD LR pacing interval to an expected A4 event time plus a delay interval to provide rate smoothing. To illustrate, rather than waiting for the VDD LR interval that may be set to 1.5 seconds for a minimum base rate of 40 pulses per minute, the pace timing circuit 242 may set a rate smoothing adjusted LR interval that is a delay interval longer than the most recent ventricular pacing cycle length. For instance, if the preceding two ventricular pacing pulses were delivered 800 ms apart (approximately 75 beats per minute), the ventricular pacing pulse delivered at block 712 may be delivered at 1000 ms, e.g., 800 ms plus a delay interval of 200 ms, if an A4 event has not been detected. In this way, some extra time is allowed for detecting the A4 event but asystole is prevented without a sudden large change in ventricular rate from 75 beats per minute to 40 beats per minute by using the adjusted LR interval of 1000 ms (60 beats per minute).

The count of A4 events detected out of a predetermined number of ventricular cycles is updated at block 711. At block 712, the control circuit 206 determines if the A4 detection count obtained over a predetermined number of ventricular cycles is less than a mode-switching threshold. A threshold number of X A4 detections out of a predetermined number of Y ventricular cycles may be required to remain in the VDD pacing mode. In various examples, control circuit 206 may determine if less than a threshold number of X A4 events have been detected for the most recent Y ventricular cycles where X and Y are equal (consecutive ventricular cycles) or where X is less than Y (non-consecutive cycles). Less than a threshold number of A4 events out of Y ventricular cycles may be set as one motion signal metric criterion for switching from the VDD atrial tracking pacing mode to a non-atrial tracking pacing mode.

The X of Y criterion may be programmable and may be based in part on the patient's history of atrial fibrillation. For example, if the patient does not have a history of atrial fibrillation, the atria may be in sinus rhythm, but the A4 event signal is not being detected. In a patient with no history of atrial fibrillation, it may be desirable to remain in the VDD pacing mode for a relatively longer period of time to enable detection of the A4 events and promote atrial-synchronized ventricular pacing. In the case of little or no history of atrial fibrillation, a relatively high number of ventricular cycles without A4 event detections may be required before switching the pacing mode. For example, less than 10 A4 event detections out of 20 ventricular cycles or less than 12 A4 event detections out of 24 ventricular cycles may be required at block 712 before switching to a non-atrial tracking pacing mode at block 718.

In a patient with a strong history of atrial fibrillation, however, it may be desirable to switch to a non-atrial tracking pacing mode relatively quickly since the loss of A4 event detection may be due to atrial fibrillation. The X of Y criteria may be set relatively less stringent compared to in a patient with no or minimal atrial fibrillation history to more rapidly switch to the non-atrial tracking pacing mode to provide ventricular rate support pacing. The X of Y criteria may be set to less than 6 A4 event detections out of 10 ventricular cycles or less than 10 A4 event detections out of 16 ventricular cycles, for example. If the count of A4 event detections out of Y ventricular cycles is less than a pacing mode switching threshold, control circuit 206 may immediately switch to a non-atrial tracking pacing mode at block 718. If the threshold number of A4 event detections is reached or exceeded, at block 712, the pacemaker 14 may remain in the VDD mode and return to block 704.

However, other mode-switching criteria may be applied for enabling control circuit 206 to switch from the VDD to a non-atrial tracking pacing mode. For example, if the X of Y pacing mode switching criterion relating to A4 event detections is not met, control circuit 206 may apply other criteria at block 716 for causing a pacing mode switch to a non-atrial tracking pacing mode. In one embodiment, the control circuit 206 may determine the patient body posture at block 714 as a motion signal metric for comparison to pacing mode switching criteria at block 716. Patient body posture may be determined from an analysis of the motion sensor signal when motion sensor 212 is implemented as an accelerometer, or a dedicated accelerometer may be included in pacemaker 14 for detecting patient body posture. Example techniques for determining patient body posture from a one-dimensional or three-dimensional accelerometer are generally disclosed in U.S. Pat. Publication No. 2015/0217119, (Sheldon, et al.), U.S. patent application Ser. No. 14/920,228 (Sheldon, et al.), both incorporated herein by reference in their entirety, and in the above-incorporated U.S. Pat. Nos. 5,593,431 and 6,044,297.

If the detected patient's body posture meets pacing mode switching criteria, as determined at block 716, the control circuit 206 switches to a non-atrial tracking pacing mode at block 718. In some patients, postural changes may influence the motion sensor signal. A particular posture may be identified in which A4 event detection is poor or unreliable for atrial tracking of ventricular pacing. The control circuit 206 may proactively switch to a non-atrial tracking pacing mode even if the number of A4 detections is greater than the pacing mode switching threshold at block 712. If the patient's body posture is determined to be a posture known to be associated with poor A4 detection, control circuit 206 may switch to the non-atrial tracking mode in anticipation of losing A4 event detection.

In other examples, the control circuit 206 may determine the patient body posture at block 714 even when the A4 event detection count is equal to or greater than the pacing mode switching threshold at block 712. In other words, the "yes" branch of block 712 may alternatively lead to block 714 for determining the patient body posture. The patient body posture mode switch criterion may require that the patient be in an upright posture before switching to the non-atrial tracking pacing mode, even when the switching criterion of less than X A4 detections out of at least Y ventricular cycles is met. If A4 events are under-detected, and the patient is upright, e.g., sitting, standing, walking, etc., ventricular rate support may be needed and can be provided by switching to the non-atrial tracking pacing mode. An upright posture is generally indicative of a non-resting posture during which the patient is assumed to be awake and may be physically active, requiring ventricular pacing support at a rate greater than the VDD lower rate. If the patient posture meets mode switching criteria at block 716, e.g., an upright position or non-resting position, control circuit 206 switches to the non-atrial tracking pacing mode at block 718.

However, if the patient posture does not meet the mode switching criteria, the pacemaker 14 remains in the VDD pacing mode, even though the A4 detection count is less than the mode switching threshold at block 712. If the patient is in a non-upright or resting position, for example in any lying or reclined position generally indicative of a sleeping or resting posture, the VDD lower rate may provide adequate ventricular rate support for the patient at rest. The VDD LR pacing interval established at block 702 allows more time for detecting an A4 event between pacing pulses than the relatively shorter non-atrial tracking LR interval. By remaining in the VDD pacing mode when the patient is at rest and not needing a higher pacing rate may promote an earlier return to A4 event detection and atrial synchronized ventricular pacing when the patient is resting. In this case, the control circuit 206 may remain in the VDD pacing mode by returning to block 704.

Figure 10B:
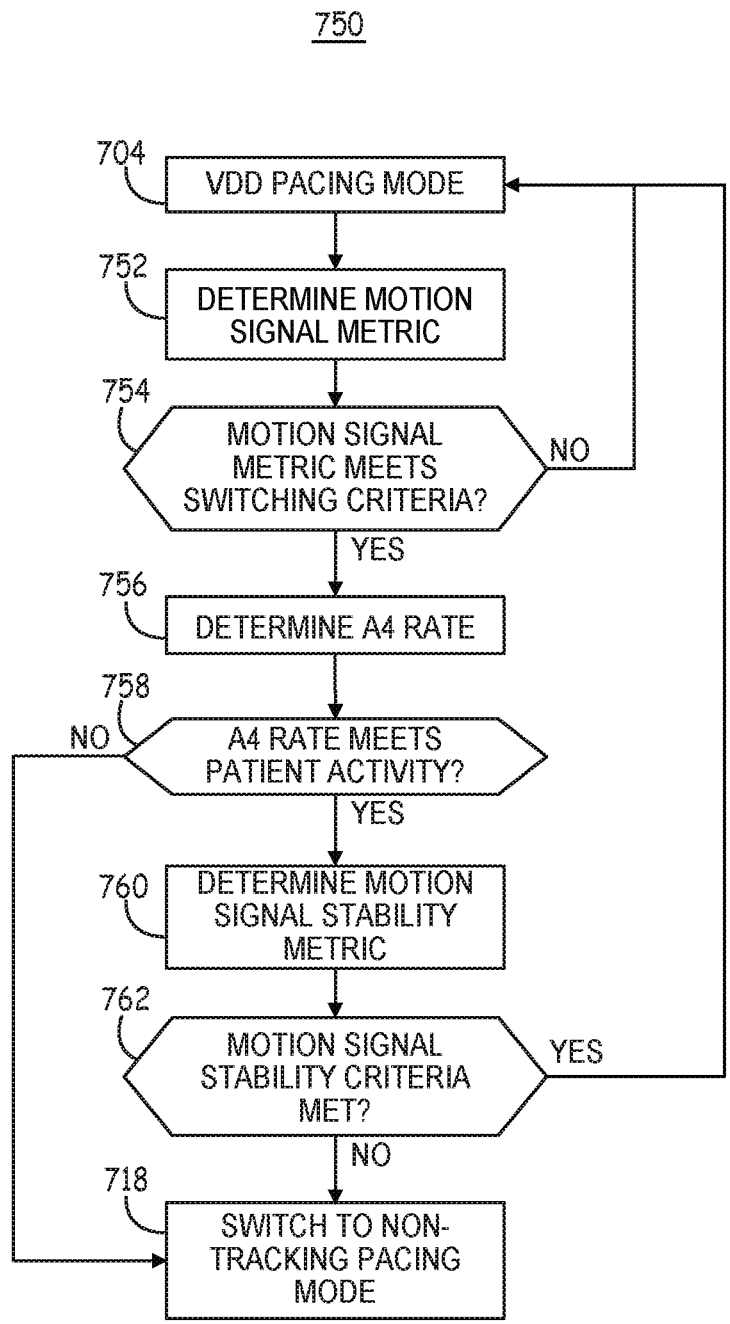
FIG. 10B is a flow chart of a method for controlling pacing mode switching from the atrial tracking pacing mode to the non-atrial tracking mode according to another example.

FIG. 10B is a flow chart 750 of a method for controlling pacing mode switching from the VDD pacing mode to a non-atrial tracking mode that may be performed by pacemaker 14 according to another example. At block 704, pacemaker 14 is operating in the VDD pacing mode. In this example, block 704 corresponds to identically-numbered block 704 of FIG. 10A to indicate that the techniques of flow chart 750 may be performed in parallel, concomitantly or sequentially to the techniques of flow chart 700. The techniques of flow chart 750 provide additional or alternative pacing mode switching criteria that may be used to control when pacemaker 14 switches from the atrial tracking pacing mode to a non-atrial tracking pacing mode. The process of flow chart 750 in FIG. 10B may be implemented on its own to control pacing mode switching based on a motion signal metric, without performing the process of FIG. 10A. In various embodiments, the processes of FIGS. 10A and 10B may be combined, the process of FIG. 10A may be performed alone without being combined with the process of FIG. 10B, or vice versa.

In FIG. 10B control circuit 206 monitors a motion signal metric, determined at block 752, for applying mode switching criteria to for determining whether to switch from VDD pacing to a non-atrial tracking pacing mode. The techniques of FIG. 10B may be implemented to cause a change in pacing mode in response to increased frequency and/or amplitude of non-cardiac motion signals due to elevated patient physical activity or motion signal noise, even if mode switching criteria relating to A4 under-detection are not satisfied in the process of FIG. 10A. The motion signal metric determined at block 752 may be a patient physical activity metric determined from one or more sensor signals that is/are correlated to patient physical activity. If motion sensor 212 is implemented as an accelerometer, an activity count or other activity metric that is correlated to patient physical activity (and patient metabolic demand) may be determined from the motion sensor signal. Methods for determining a patient activity metric from an accelerometer included in pacemaker 14 are generally disclosed in the above-incorporated U.S. patent application Ser. No. 14/920,228 (Sheldon, et al.) and U.S. Pat. Publication No. 2016/0144191 (Sheldon, et al.), also incorporated herein by reference in its entirety.

When pacemaker 14 is operating in the atrial-tracking VDD pacing mode, determining patient physical activity and a corresponding SIR for providing a rate responsive pacing rate is not required. However, determination of at least a patient activity metric and optionally a SIR may be performed by control circuit 206 during the VDD pacing mode for use in determining if pacing mode switching criteria are satisfied at block 754.

Other motion signal metrics that may be used for determining if switching criteria are met may include a metric indicating patient posture or a metric determined from a predetermined time segment of the motion signal by processing sample points over the predetermined time segment to obtain a metric indicative of the signal energy, signal entropy, or noise. A motion signal metric determined by processing motion signal sample points over a predetermined time segment may indicate that A4 event sensing is likely unreliable due to increased frequency and/or amplitudes of non-cardiac signals in the motion signal during the predetermined time segment. The motion sensor metric may be determined by summing the absolute amplitudes of successive motion signal sample points over a predetermined time segment or during a specified window, e.g., during an A3 sensing window, during the A4 refractory period, outside the A4 refractory period, during an A4 window, during an A4-A4 cardiac cycle, during a ventricular cardiac cycle, or during a time segment defined independent of the timing of cardiac events. Average slope, average amplitude, mean frequency, or other motion signal metrics may be determined that are indicative of an increased motion signal energy that may interfere with reliable A4 event sensing.

At block 754, control circuit 206 may compare the motion signal metric to a motion signal metric threshold for triggering pacing mode switching. If the motion signal metric is determined as a patient physical activity metric, the patient physical activity metric may be compared to pacing mode switch activity threshold. Comparison of the patient activity metric to a mode switching threshold may be performed each time the patient activity metric is determined or on a less frequent basis. In one example, the patient activity metric is determined from the motion sensor signal at regular time intervals, e.g., every two seconds, every six seconds, every thirty seconds, every minute, etc. The patient activity metric may be determined from the motion sensor signal that is also being used for detecting A4 events. If the patient's physical activity is increased, resulting in increased frequency of signal spikes in the motion sensor signal that are caused by patient body motion (other than cardiac motion), these patient physical activity signals may be falsely detected as A4 events. In some cases, the A4 event may move earlier in the ventricular cycle as the atrial rate increases and be under-detected during the atrial refractory period or become fused with the A3 event and more difficult to detect. As patient physical activity is increased, the control circuit 206 may switch to a non-atrial tracking pacing mode in order to provide ventricular pacing rate support appropriate for the patient's level of physical activity, independent of A4 event sensing from the motion sensor signal, which may be less reliable during the elevated patient activity.

One or a combination of metrics may be determined and compared to pacing mode switching criteria at block 754. In one example, if a patient physical activity metric is determined as the motion signal metric and is greater than a mode switch activity threshold at block 754, control circuit 206 may advance directly to block 718 to switch to the non-atrial tracking pacing mode. The patient physical activity metric may be determined as a SIR. For instance, if an activity count is determined from the motion sensor signal as described in the above-incorporated references, a transfer function may be used to convert the activity count to a SIR. The SIR may be compared to a mode switch activity threshold at block 754. The mode switch activity threshold may be a SIR corresponding to a particular level of patient physical activity, e.g., activities of daily living (such as driving, moving about the house, etc.) or a higher level of patient physical activity that occurs with exercise or physical exertion greater than every day activities of daily living. For instance, the pacing mode switch threshold may be a SIR of 90 pulses per minute. In another example the pacing mode switch threshold is a SIR of 100 pulses per minute. If a SIR is determined at block 752 as a motion signal metric and exceeds the pacing mode switch activity threshold at block 754, the pacemaker 14 may immediately switch to the non-atrial tracking pacing mode at block 718.

Other motion signal metrics may be compared to respective pacing mode switching thresholds in addition to or alternatively to a patient physical activity metric. For example, a summation of amplitudes, mean amplitude, mean slope, mean frequency or other motion signal metric may be compared to a respective pacing mode switching threshold. If the threshold is reached, A4 event sensing may be deemed unreliable and the process may advance directly to block 718 to switch to a non-atrial tracking pacing mode.

In the example shown, however, control circuit 206 may analyze the A4 event rate and/or motion sensor signal stability in response to the motion signal metric meeting pacing mode switching criteria at block 754. As such, control circuit 206 may be configured to determine the A4 event rate at block 756. The A4 event rate may be determined by determining the time interval between a detected A4 event and the most recent preceding A4 event as the A4 event interval. One or more A4 event intervals may be determined and averaged for comparison to the SIR or compared individually to the SIR pacing interval to determine if the A4 event rate matches the SIR within an acceptable range, e.g., ±10 beats per minute. Three, five, eight or other predetermined number of A4 event intervals may be averaged or compared individually to the SIR interval. For example, if the SIR is determined to be 120 pulses per minute, which may be set as a maximum upper pacing rate, the SIR pacing interval is 500 ms. If the average of two or more A4 event intervals is greater than or less than 500 ms by more than an acceptable rate response threshold margin, e.g., greater than 600 ms or less than 400 ms, the A4 rate may be determined to not meet the patient's physical activity demand at block 758.

In other examples, M out of the most recent N A4 event intervals may be required to be within a threshold margin of the SIR pacing interval, e.g., within 10%, 20% or other percentage of the SIR pacing interval. The threshold margin may be a variable margin that allows larger differences between the SIR pacing interval and the A4 event intervals at relatively lower SIRs and relatively smaller differences between the SIR pacing interval and the A4 event intervals at relatively higher SIRs when the demand for pacing rate support may be more critical for preventing the patient from becoming symptomatic. For example, if the SIR is within a range corresponding to activities of daily living, e.g., a pacing rate of 80 beats per minute (temporary LR interval of 750 ms), the threshold margin may be 20% so that if the A4 event intervals are between 600 ms and 900 ms, the A4 event rate is determined to meet the patient activity demand at block 758. If the SIR is greater than a range corresponding to activities of daily living, indicating patient exertion, the threshold margin may be 10%. If the SIR is 100 pulses per minute (600 ms temporary LR interval), for example, the A4 event intervals may be required to fall between 540 ms to 660 ms to meet the patient physical activity demand at block 758.

If A4 events are being detected and are occurring at a rate that supports the patient's current physical activity demand as determined at block 758, which may be based on a comparison of the A4 event rate to the SIR, the pacemaker 14 may remain in the atrial tracking VDD pacing mode to continue atrial-synchronized ventricular pacing by appropriately tracking the atrial rate. If the A4 event rate is slower or faster than the SIR by a predetermined margin, A4 event tracking for controlling ventricular pacing is no longer providing the ventricular pacing rate support appropriate to match the patient's physical activity demand. Control circuit 206 may switch to the non-atrial tracking pacing mode at block 718.

Additionally or alternatively, control circuit 206 may determine if the motion sensor signal stability meets pacing mode switching criteria. If the A4 event rate meets or matches the patient physical activity demand at block 758, control circuit 206 may determine a motion sensor stability metric at block 760. In other examples, if the motion signal metric meets the switching criteria at block 754, the motion signal stability metric may be determined at block 760 without checking the A4 event rate (omitting blocks 756 and 758 in some examples).

In one example, the motion sensor stability metric is the A4 event amplitude. Stability of the A4 event amplitude is an indication that reliable A4 event detection is likely and, as such, the VDD pacing mode is still appropriate. A large variation of the A4 event signal amplitude may indicate false A4 event detections, e.g., due to patient physical activity signal spikes being falsely detected as A4 events, and a loss of reliable A4 event sensing for the purpose of atrial tracking in the VDD pacing mode.

The motion sensor signal stability metric may be determined at block 760 by determining differences between the peak amplitude of each one of a predetermined number of detected A4 events and a moving average A4 event amplitude or other previously determined statistical measure of A4 event amplitude. In another example, a cumulative amplitude difference between successively detected A4 events may be determined at block 760 by determining the absolute value of the difference between the current A4 event amplitude and the most recent preceding A4 event amplitude and summing the absolute values of the differences determined for three or more consecutively determined A4 event amplitude differences. If the cumulative amplitude difference is greater than a stability threshold, the motion sensor signal is determined to not meet stability criteria required to remain in the VDD pacing mode. In other examples, M out of N most recent A4 events may be required to be within an amplitude difference threshold of each other or an average A4 event amplitude of the N events.

Other features of detected A4 events may be determined at block 760 and analyzed for determining if motion sensor signal stability criteria are satisfied at block 762. For example, A4 event interval variability or A4 timing relative to the preceding ventricular pacing pulse, sensed R-wave or a ventricular mechanical event (e.g., A1, A2 or A3 event) may be determined to evaluate whether the A4 event is stable or presenting an expected trend (such as gradually moving earlier in the ventricular cycle) relative to ventricular events. The slope, width, polarity or other morphological features of the A4 event may be determined for a comparative analysis at block 762 to evaluate the stability of the A4 event feature as an indication of true A4 event detections as opposed to false A4 event detections.

Other motion sensor signal stability metrics may be determined at block 760 relating to the A1, A2 and/or A3 events in addition to or alternatively to A4 event features. Criteria applied at block 762 for confirming motion sensor signal stability may include stability of A1, A2, and/or A3 morphology features and/or timing. It is recognized that numerous comparative analyses may be performed to apply criteria for determining stability and consistency of the cardiac mechanical signals of the A1, A2, A3 and/or A4 events to increase the confidence that the detected A4 events are true A4 events and not signal peaks caused by patient physical activity or other non-cardiac motion or motion sensor signal noise.

If the motion sensor signal stability criteria are not met at block 762, control circuit 206 switches to a non-atrial tracking pacing mode at block 718. If the A4 event rate meets the patient physical activity demand ("yes" branch of block 758) and the motion sensor signal stability criteria are met at block 762, pacemaker 14 remains in the VDD pacing mode at block 704.

The foregoing examples of determining if the A4 rate meets a patient physical activity demand at block 758 and if the motion sensor signal stability meets stability criteria at block 762 are provided for illustrative purposes and are not intended to be limiting. It is recognized that other threshold margins and rate threshold criteria may be applied at block 758 for determining if the detected A4 rate matches the metabolic need of the patient for the purposes of tracking the A4 rate in providing ventricular pacing. When the A4 rate is too low (or too high) compared to the patient activity-based SIR, atrial tracking of the ventricular pacing rate does not provide a ventricular rate that matches the patient's metabolic need. As such, a switch to the non-atrial tracking pacing mode is warranted at block 718 when the A4 rate does not meet the SIR rate according to criteria applied at block 758.

Furthermore, motion signal stability criteria may be applied whether or not the A4 event rate meets the patient physical activity demand at block 758 in other examples. In some cases, if the motion signal stability criteria are not met at block 762, even if the A4 event rate matches the patient's physical activity at block 758, control circuit 206 may switch to a non-atrial tracking pacing mode at block 718.

Figure 11:
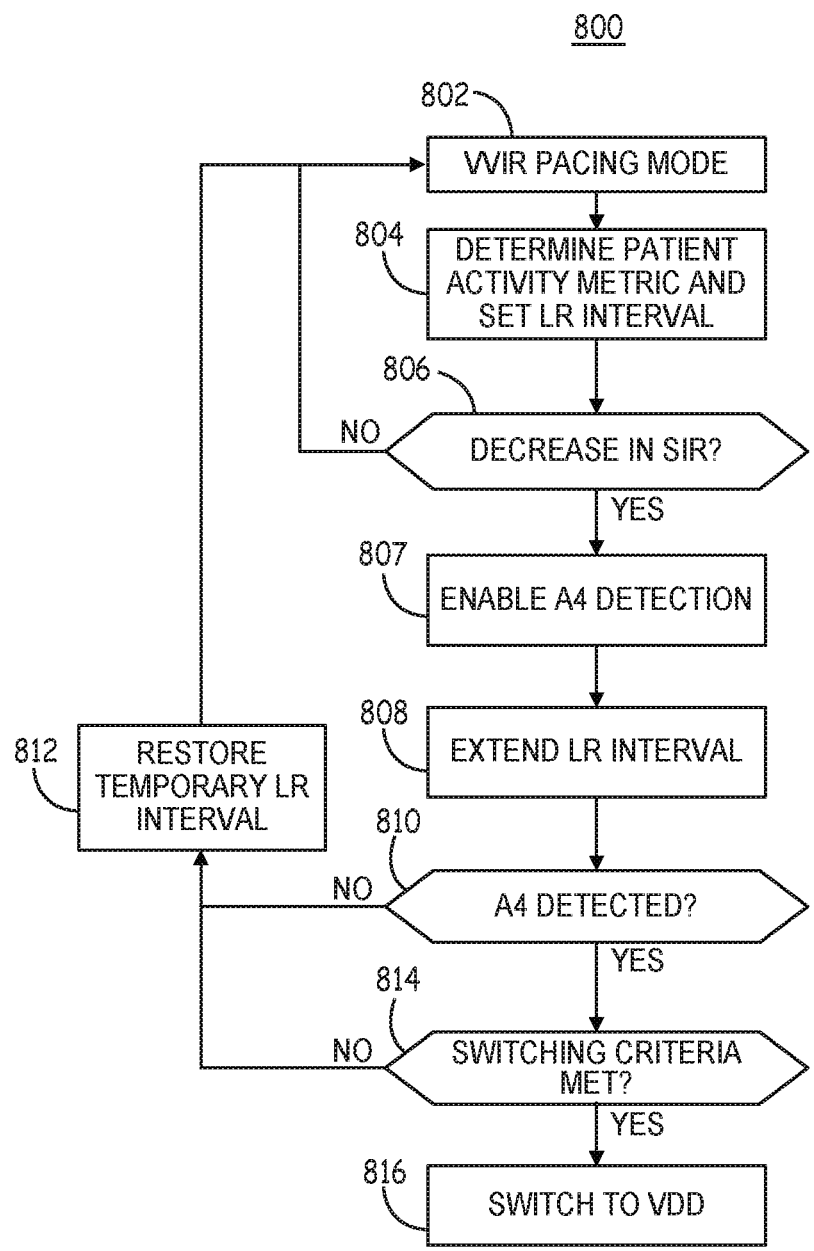
FIG. 11 is a flow chart of a method for controlling pacing mode switching from a non-atrial tracking pacing mode to an atrial tracking pacing mode in an intracardiac pacemaker according to one example.

FIG. 11 is a flow chart 800 of a method performed by pacemaker 14 for controlling pacing mode switching from a non-atrial tracking pacing mode back to an atrial tracking pacing mode according to one example. At block 802, pacemaker 14 is operating in a non-atrial tracking pacing mode. In this example, the non-atrial tracking pacing mode is a VVIR pacing mode. The VVIR pacing mode of block 802 may be arrived at in response to pacing mode switching criteria being met during the VDD pacing mode of FIG. 10A or FIG. 10B. For example, the VVIR pacing mode 802 may be started in response to A4 under-detection and/or patient posture-based mode switching criteria as described in conjunction with FIG. 10A or in response to a motion signal metric, A4 rate mismatch with physical activity, and/or motion sensor signal stability as described in conjunction with FIG. 10B.

During the VVIR pacing mode, A4 event detection is disabled most of the time, which conserves pacemaker battery longevity. A4 event detection may be disabled, for example, by powering down atrial event detector circuit 240 or disabling processing functions performed for detecting A4 events. The motion sensor 212, however, may remain enabled for producing a motion sensor signal for use by control circuit 206 for determining a patient physical activity metric and SIR for controlling the ventricular pacing rate during VVIR pacing. A4 event detection from the motion sensor signal may be periodically enabled to determine if mode switching criteria relating to A4 event detection are satisfied for switching back to the VDD pacing mode.

In FIG. 11, a patient activity metric is determined at block 804 for determining the SIR for controlling the VVIR pacing rate. The patient activity metric determined at block 804 may be equivalent to a patient activity metric determined at block 752 of FIG. 10B as a motion signal metric, but could be a different metric. The SIR is determined from the patient activity metric, and pacemaker 14 sets the ventricular LR interval according to the SIR. The LR interval may be set to a temporary LR interval, shorter than the base rate LR interval, to provide ventricular pacing at the SIR.

At block 806, control circuit 206 determines if the SIR based on the patient activity metric has decreased from a previously determined SIR. The previously determined SIR may have been determined during the VDD pacing mode and led to pacing mode switching to the VVIR pacing mode. In other cases, the previously determined SIR may be determined after switching to the VVIR pacing mode. If a decrease in the SIR since a previously-determined SIR is detected, A4 event detection may be enabled at block 807 during the VVIR pacing mode. A4 event detection may be enabled for one or more ventricular pacing cycles.

After enabling A4 event detection, in order to promote detection of the A4 event, the LR pacing rate interval may be extended at block 808 to a longer pacing interval than the LR interval set according to the currently determined SIR. For example, if the SIR is initially at 100 pulses per minute (ppm) and drops to 90 ppm, the temporary LR interval may be increased from 600 ms (SIR of 100) to 670 ms (SIR of 90). The temporary LR interval of 670 ms may be extended at block 808 by predetermined extension interval or adjusted to decrease the heart rate by 10 beats per minute or other rate less than the SIR. In the above example of a SIR of 90 and LR interval of 670 ms, the temporary LR interval may be extended to 750 to 1000 ms (pacing rate between 80 and 60 ppm) to allow more time for the A4 event to be detected during the extended LR pacing interval. In one example, the pacing rate is decreased by 10 ppm below the SIR, from 90 ppm to 80 ppm in the above example, for a predetermined number of pacing cycles.

The likelihood of detecting an A4 event before the next ventricular pacing pulse is increased by extending the LR interval by 50, 100, 200 or even up to 500 ms or longer for one or more pacing cycles at block 808. In some examples, a temporary LR interval may be extended at block 808 by a fixed extension interval, e.g., 100 ms, on one or more pacing cycles. In other examples, a temporary LR interval may be increased by a successively increasing extension interval on each one of a predetermined number of consecutive pacing cycles. To illustrate, a temporary LR interval may be increased by an extension interval that increases by 50 ms on each successive pacing cycle, e.g., extension intervals of 50 ms, 100 ms, 150 ms, 200 ms and 250 ms may be added to the temporary LR interval on each respective one of five consecutive pacing cycles to promote A4 detection. Alternatively, the pacing interval may be successively increased until the A4 event is detected up to a maximum extension interval. If an A4 event is detected, the extended LR interval at which the A4 event was first detected may be maintained for a predetermined number of ventricular pacing cycles for determining if reliable A4 event detection has returned. A maximum extension of the temporary LR interval may be limited by the currently determined SIR to avoid a mismatch between patient metabolic need and the ventricular pacing rate.

It is recognized that if the SIR has decreased to a base pacing rate (minimum VVIR pacing rate) at block 806, a temporary LR pacing interval set for the previously determined SIR is adjusted to the permanent LR interval established for the non-atrial tracking mode at block 702 of FIG. 10A. For example, if the patient activity metric falls to a resting level, e.g., less than an activities of daily living threshold, the VVIR permanent LR pacing interval may be in effect at block 804. The VVIR LR interval may be extended, e.g., to the VDD LR interval or intermediate to the VDD LR and the VVIR LR interval. In other examples, if the SIR is at the base or minimum pacing rate, e.g., 60 ppm, the VVIR LR interval may not be extended at block 808 in order to maintain the heart rate at the minimum VVIR pacing rate. As such, in some examples a temporary LR interval set based on a non-resting SIR may be extended at block 808, but the LR interval set during a SIR equal to the base pacing rate is not extended at block 808.

If A4 events are not detected during the one or more extended LR pacing intervals, "no" branch of block 810, the extended LR interval is adjusted back to the permanent or temporary LR interval corresponding to the currently-determined SIR at block 812. If at least one A4 event, or other predetermined threshold number of A4 events, is detected at block 810, control circuit 206 may determine if pacing mode switching criteria are met at block 814. The pacing mode switching criteria applied at block 814 may require that a threshold number of A4 events are detected during consecutive or non-consecutive ventricular pacing cycles. The A4 events may be detected during the temporary LR interval, the permanent LR, or during the extended LR rate interval to meet an X A4 events out of Y ventricular cycles criterion. The X of Y criterion applied at block 814 may be defined the same or differently than the X of Y criterion applied at block 712 of FIG. 10A for determining if A4 under-detection is occurring during the VDD pacing mode for controlling switching from atrial tracking to the non-atrial tracking pacing mode.

In some examples, the X of Y criteria may be conditional criteria that are defined differently for different conditions, such as different patient activity levels, and/or different patient body postures. The X of Y criteria may be defined to require relatively low threshold number of A4 event detections, e.g., 4 out of 8 ventricular cycles or 8 out of 16 ventricular cycles, to promote switching to the VDD pacing mode when the patient physical activity is low and/or when the patient posture is a resting posture, e.g., a lying or non-upright, resting posture. The X of Y criteria may be defined relatively low to promote switching to the VDD pacing mode when the patient body posture is known to be associated with reliable A4 event sensing (or at least not associated with unreliable A4 event sensing).

The X of Y criterion may be defined relatively high, e.g., 14 A4 event detections out of 16 ventricular cycles, to be biased toward remaining in the non-atrial tracking pacing mode when the patient physical activity is high and/or the patient body posture is upright. The X of Y criteria may be defined to be relatively high to be biased toward remaining in the non-atrial tracking pacing mode when the patient body posture is known to be associated with unreliable A4 event detection. As such, X of Y criteria may be applied at block 814 requiring at least or greater than a threshold number of A4 event detections out of Y ventricular cycles to be detected where the threshold number of A4 events is determined by control circuit 206 based on patient physical activity and/or patient body posture. The X of Y criterion used under particular activity and/or posture conditions may be retrieved from memory 210, e.g., from a look-up table stored in memory 210.

Other pacing mode criteria may be applied at block 814 in addition to or alternatively to at least a threshold number of A4 event detections. For example, the rate of the detected A4 events may be required to be within a predetermined range of the currently determined SIR, the patient activity metric or SIR may be required to be below a threshold activity level, and/or the patient posture may be determined and required to match a posture known to be associated with reliable A4 event sensing (or at least not match a posture known to be associated with unreliable A4 event sensing). Motion sensor stability criteria may also be applied at block 814 to increase the confidence in reliable A4 event detection prior to switching back to VDD pacing. One or more other motion signal metrics may be determined and compared to mode switching criteria at block 814, such as a mean motion signal amplitude, frequency, slope or other signal feature determined over a predetermined time segment of the motion signal. The motion signal metric may be compared to a threshold value for switching back to VDD pacing. For example, a metric of the motion signal energy, entropy, frequency or other metric that includes non-cardiac motion signals in the motion signal may be determined and be required to be below a corresponding threshold value in order to rely on A4 event detection for controlling the atrial tracking pacing mode.

In the example of FIG. 11, A4 detection is required at block 810 during the non-atrial tracking pacing mode prior to switching back to the VDD pacing mode at block 816. As such, A4 event detection which is disabled during the VVIR pacing mode is temporarily enabled. In other examples, however, control circuit 206 may switch back to the VDD pacing mode at block 816 in response to other mode switching criteria being met without requiring A4 event detection during the VVIR pacing mode. A4 event detection may remain disabled throughout the VVIR pacing mode. For example, a motion signal metric may be periodically determined at block 814 during the VVIR pacing mode without determining if A4 event detection has returned. The motion signal metric, which may be the patient physical activity metric or another motion signal metric as described above in conjunction with FIG. 10B, may be compared to a mode switching threshold at block 814. Control circuit 206 may switch back to the VDD pacing mode at block 816 and then re-enable A4 event detection.

In another example, if control circuit 206 detects a resting level of activity based on a patient activity metric or the SIR and/or detects a lying or resting, non-upright posture at block 814, control circuit 206 may switch to the VDD pacing mode without enabling A4 event detection during the VVIR pacing mode. Ventricular pacing may be delivered at the VDD base rate (permanent VDD LR interval) as needed until A4 event detection is regained. Rate smoothing may be applied to arrive at the VDD base rate from the last VVIR pacing rate.

Figure 12:
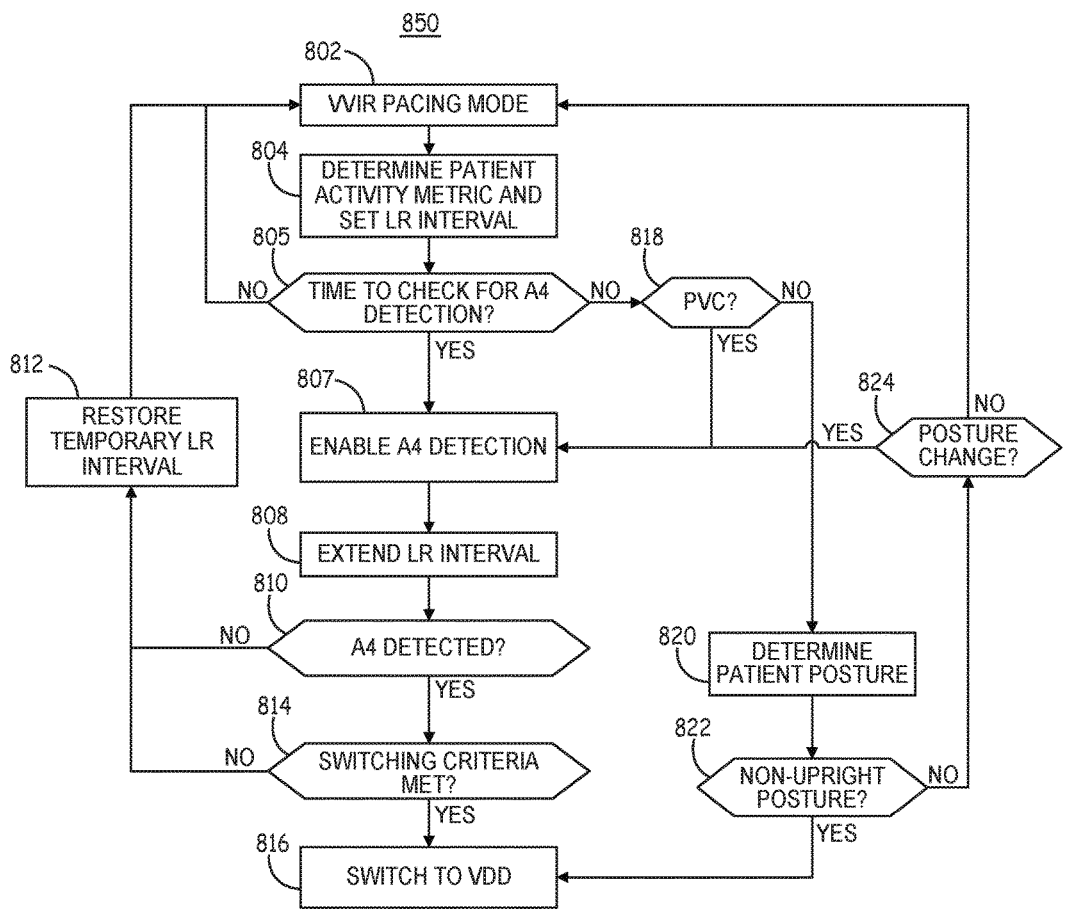
FIG. 12 is a flow chart of a method that may be performed for controlling pacing mode switching from a non-atrial tracking mode to an atrial tracking mode according to another example.

FIG. 12 is a flow chart 850 of a method that may be performed by pacemaker 14 for controlling pacing mode switching from a non-atrial tracking mode to an atrial tracking mode according to another example. Blocks 802, 804, and 808 through 816 generally correspond to identically numbered blocks described above in conjunction with FIG. 11. The techniques of FIG. 11 and FIG. 12 may be performed independently or combined.

In the example of FIG. 12, instead of waiting for a decrease in SIR before enabling A4 event detection, control circuit 206 may periodically enable A4 event detection at block 807 based on a predetermined, scheduled basis as determined at block 805. The periodic A4 event monitoring may be scheduled at a predetermined frequency. The frequency may be a predetermined number of ventricular pacing pulses (or combination of ventricular pacing pulses and sensed R-waves) or a predetermined time interval. For example, A4 event detection may be checked after every 16, 24, 30 or other predetermined number of pacing pulses. The temporary LR interval may be extended at block 808 to decrease the ventricular pacing rate by 10 ppm after every 16 pacing pulses in one example. In other examples, A4 event detection may be scheduled every minute, every thirty minutes, every hour or other scheduled time interval.

In some examples the frequency of the periodic monitoring may be dependent on the SIR and/or the condition that led to switching from VDD to the VVIR pacing mode. For example, as the SIR decreases, more frequent monitoring for A4 events may be enabled than when the SIR is high. To illustrate, if the SIR is at the maximum pacing rate, e.g., 120 ppm, A4 event monitoring may only be enabled if the SIR decreases from the maximum pacing rate as described above in conjunction with FIG. 12. If the SIR is greater than 100 ppm but less than the maximum 120 ppm, A4 event monitoring may be performed every five minutes. If the SIR is greater than 80 and less than 100 ppm, A4 event monitoring may be performed more frequently, e.g., every two minutes. If the SIR drops below the activities of daily living rate, e.g., 80 ppm or less, A4 event monitoring may be performed every minute to promote switching back to VDD pacing when pacing support at a high rate is no longer needed and when reliable A4 event detection is more likely during the relatively longer pacing intervals and physical activity is contributing less to the motion sensor signal. A4 event detection may be enabled when the SIR decreases by a threshold amount, as described in conjunction with FIG. 11, and then be scheduled to be re-enabled at a predetermined frequency.

In other examples, control circuit 206 may determine that is it time to check for A4 detection at block 805 and enable A4 event detection at block 807 at a frequency that is determined based on the reason for switching from the VDD pacing mode to the VVIR pacing mode. For instance, if control circuit 206 switched from the VDD pacing mode to the VVIR pacing mode due to A4 signal instability, A4 event monitoring may be enabled relatively frequently, e.g., once per minute, since transient motion sensor signal noise may have caused the A4 signal instability.

At any time during the VVIR pacing mode, if a premature ventricular contraction (PVC) is detected (block 818), the pace timing circuit 242 may extend the temporary LR interval at block 808 to allow for A4 event detection during the long compensatory pause that follows a PVC. The temporary LR interval may be extended to the programmed permanent LR interval or other back-up pacing interval to allow a relatively long time interval for detecting an A4 event. If an A4 event is detected at block 810, during the long compensatory pause following a PVC, additional extended LR intervals may be applied to determine if at least X of Y A4 event detections are made and/or other mode switching criteria (e.g., posture, activity level, SIR, motion signal stability and/or other motion signal metric) may be checked at block 814 as described above in conjunction with FIG. 11.

As such, in some examples, A4 event detection is enabled at block 807 during the VVIR pacing mode in response to detecting a PVC. The PVC may be detected from the cardiac electrical signal based on the time of an R-wave sensed event following a preceding ventricular pacing pulse or sensed R-wave and/or based on an analysis of the R-wave morphology according to a PVC detection algorithm implemented in pacemaker 14.

In the example of FIG. 12, control circuit 206 may determine the patient body posture at block 820. Control circuit 206 may monitor patient body posture for detecting a non-upright posture (indicative of a resting state) and/or for detecting a posture change. Patient body posture determination may be performed periodically on a scheduled basis and/or in a response to a change in SIR. If a resting body posture is detected at block 822, control circuit 206 may switch to the VDD pacing mode. A resting body posture may be detected when any lying posture or reclined posture is detected as opposed to an upright sitting, standing, walking or running posture is detected. Such upright postures may be collectively referred to as non-resting body postures.

Ventricular rate support may not be required in a resting posture. In some examples, in addition to detecting a resting body posture, control circuit 206 may verify that the patient activity metric or SIR are at a resting level, e.g., less than an activities of daily living threshold. Control circuit 206 may proactively switch to the atrial tracking VDD pacing mode at block 816 when the patient is anticipated to be in a resting state based on a non-upright body posture.

Verification of A4 event detection prior to switching to the VDD pacing mode may not be required. The ventricular pacing rate may be adjusted down toward the VDD lower rate until A4 event detection and atrial-synchronized ventricular pacing is restored. As such, in some examples, pacing mode switching criteria applied during the VVIR pacing mode may not require enabling A4 event detection. The decision to switch back to the VDD pacing mode may be made by control circuit 206 based on other analysis of the motion sensor signal, e.g., patient physical activity and/or body posture and/or motion sensor metric, without enabling A4 event detection.

If patient body posture is determined to be a non-resting or upright position, "no" branch of block 822, control circuit 206 may determine if the patient's body posture has changed at block 824 since a previously determined body posture. If no change in body posture is detected, pacemaker 14 remains in the VVIR pacing mode (block 802). If a change in body posture is detected, "yes" branch of block 824, control circuit 206 may advance to block 807 to enable A4 event detection and extend the temporary LR interval at block 808 to look for the A4 event. A change in body posture may influence the motion sensor signal. In some body positions the A4 event signal may have a lower signal-to-noise ratio than in other body positions. As such, a change in patient body posture may restore reliable A4 event sensing if A4 events were being under-detected in the previous body posture.

If an A4 event is detected at block 810 after detecting a posture change, mode switching criteria may be applied at block 814. The mode switching criteria may generally require a motion signal metric to meet a corresponding threshold requirement for switching back to the VDD pacing mode. The motion signal metric may be required to be greater than or less than a corresponding threshold. For example, a motion signal metric indicative of the signal energy or signal entropy may be required to be less than a corresponding threshold. In other examples, the mode switching criteria may include requiring greater than a threshold number of X undetected A4 events out of Y ventricular cycles as described previously herein. The X of Y criteria may be dependent on the determined posture. If a posture is detected that is known to be associated with reliable A4 event detection, the X of Y criteria may be relatively low, e.g., five A4 event detections out of eight consecutive ventricular cycles. If the posture change detected at block 824 is a change to a body posture that is associated with unreliable A4 event detection, or is unknown to be associated with reliable A4 event detection, higher X of Y criteria may be required, e.g., 12 out of 15 or 18 out of 22. In this way, the mode switching criteria may be biased toward returning to an atrial tracking pacing mode more rapidly when the patient's body posture is determined to be associated with reliable A4 event sensing and less rapidly when the patient's body posture is associated with unreliable A4 event sensing or unknown reliability of A4 event sensing.

Accordingly, it is to be understood that A4 event monitoring may be enabled on a periodic scheduled basis and/or in response to triggering events, such as a PVC detection, posture change, and/or decrease in SIR as described in conjunction with FIGS. 11 and 12. The mode switching criteria applied at block 814 of FIGS. 11 and 12 may be conditional criteria that are biased (set relatively low) to promote pacing in the VDD mode when A4 detection is expected to be reliable and/or when ventricular pacing in a rate responsive mode to provide ventricular rate support is not required (e.g., during resting activity and/or resting posture) and biased (set relatively high) to promote pacing in the VVIR pacing mode when A4 event detection is expected to be unreliable (e.g., during certain postures) and/or ventricular rate support is needed during a non-resting physical activity level and/or non-resting patient posture.

Furthermore, mode switching criteria for controlling switching from the VVIR pacing mode back to the VDD pacing mode may be defined so as not to require enabling A4 event detection during the VVIR pacing mode. In some examples, mode switching criteria applied during the VVIR pacing mode may be based solely on patient activity, solely on patient posture, solely on a motion signal metric determined over a predetermined time interval that is not necessarily an indicator of patient activity or patient posture, or based on a combination of two or more of the patient physical activity, patient posture, or other motion signal metrics without requiring A4 event detection for satisfying the pacing mode switching criteria for switching back to the VDD pacing mode.

Figure 13:
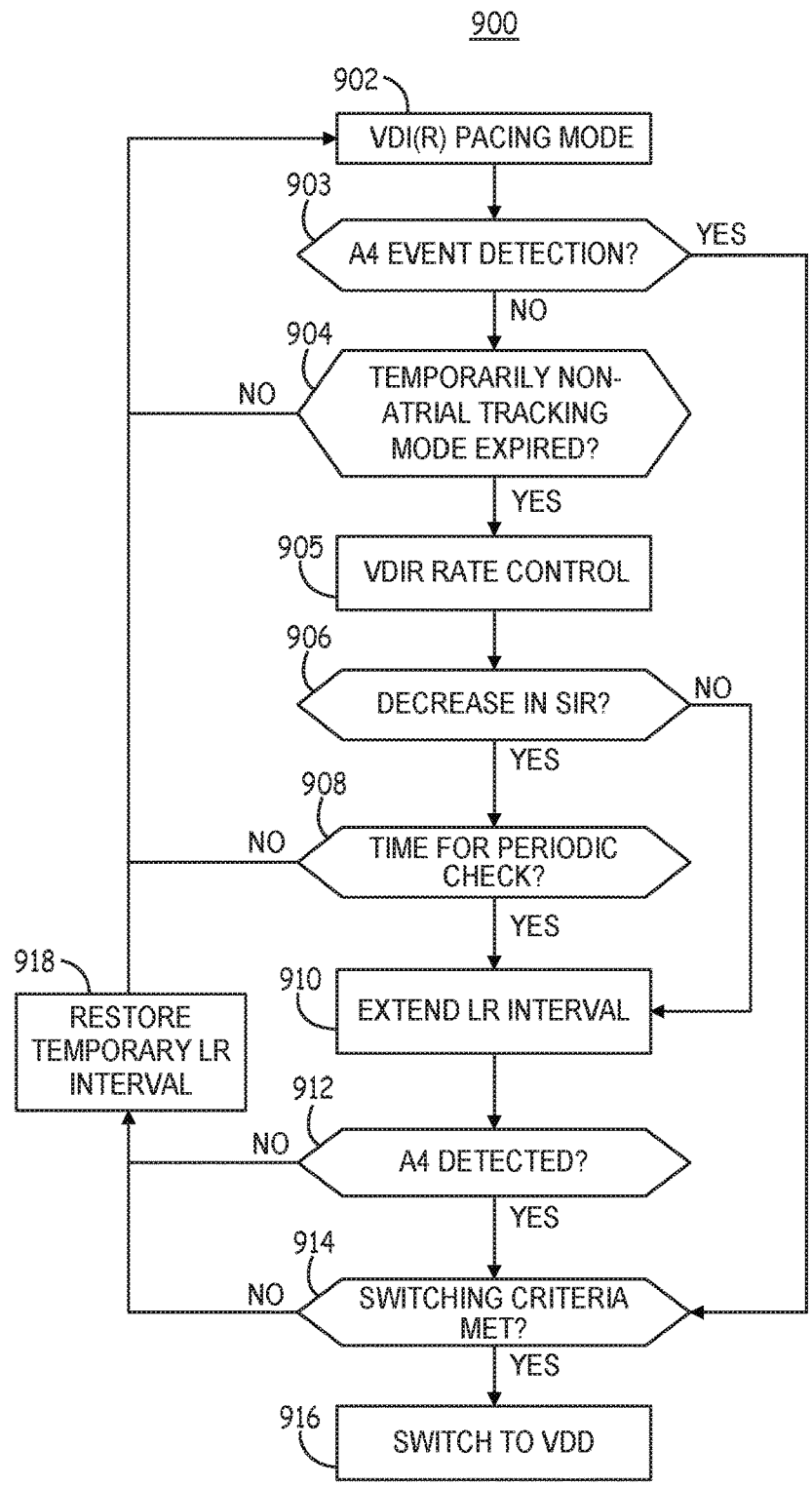
FIG. 13 is a flow chart of a method for controlling pacing mode switching by an intracardiac ventricular pacemaker according to yet another example.

FIG. 13 is a flow chart 900 of a method for controlling pacing mode switching by pacemaker 14 according to another example. When mode switching criteria are satisfied for switching from the VDD pacing mode to a non-atrial tracking pacing mode (block 718 of FIG. 10A or FIG. 10B), the control circuit 206 may switch from the VDD pacing mode to a VDIR pacing mode, rather than the VVIR pacing mode described in conjunction with FIGS. 11 and 12.

At block 902 of FIG. 13, pacemaker 14 operates in a VDIR pacing mode. Similar to the VVIR pacing mode, non-atrial tracking ventricular pacing is delivered in a rate responsive pacing mode during the VDIR pacing. Ventricular pacing pulses are delivered at a temporary LR interval set according to an SIR and inhibited when an intrinsic R-wave is sensed prior to expiration of the LR interval. One difference between the VVIR pacing mode and the VDIR pacing mode is that A4 event detection remains enabled for atrial mechanical systolic event sensing in the VDIR pacing mode. A4 event detection is disabled upon switching to the VVIR pacing mode but may be re-enabled periodically to check for A4 event detection as described above in conjunction with FIGS. 11 and 12.

If an A4 event is detected during the VDIR pacing mode, at block 903 of FIG. 13, the A4 event does not trigger a ventricular pacing pulse. A4 event detection is used for determining if pacing mode switching criteria are satisfied (block 914) but is not used for scheduling ventricular pacing pulses during the VDIR pacing mode. If an A4 event is detected at block 903, control circuit 206 may determine if a threshold number X A4 events have been detected out of the most recent Y ventricular cycles at block 914. If A4 event detection has become reliable based on the X of Y criterion being met, pacemaker 14 may switch back to VDD pacing at block 916.

The X of Y criterion may be a conditional criterion that is set based on the SIR, patient posture or other factors. For example, the X of Y criterion may be set scaled to the patient activity metric or SIR so that more A4 event detections are required with increasing patient physical activity before switching back to the VDD pacing mode.

In some examples, a patient body posture criterion and/or patient physical activity criterion or other motion signal metric may be required to be met at block 914 when A4 event detection criteria have been satisfied prior to switching to VDD pacing. For example, if an X of Y A4 event detection criterion is satisfied, control circuit 206 may verify that the patient posture is not a posture associated with unreliable A4 event detection and/or the SIR or other motion signal metric is not greater than a mode switching limit. If the patient is in a posture that is associated with unreliable A4 event detection or the SIR is greater than an activities of daily living SIR or other threshold activity level, pacemaker 14 may remain in the VDIR pacing mode by returning to block 902.

In some examples, motion sensor signal stability criteria may be required to be satisfied at block 914 before switching back to VDD pacing. Motion sensor signal stability requirements described above in conjunction with block 758 of FIG. 10B for remaining in a VDD pacing mode may be applied at block 914 for satisfying mode switching criteria for switching back to the VDD pacing mode. For example, an A4 event time interval, A4 event amplitude, A4 event slope, A4 event width or other A4 event feature or combination of features may be verified to be stable within predetermined limits over multiple ventricular cycles before control circuit 206 switches to the VDD pacing mode. In other examples, any combination of one or more time intervals and/or morphological features of any of the A1, A2, A3 and A4 events may be analyzed to determine if the motion sensor signal is stable.

In some examples, control module 206 may control switching to the non-atrial tracking pacing mode at block 718 OF FIG. 10A or 10B by first switching to a temporary non-atrial tracking pacing mode at a ventricular pacing rate that is based on a most recently determined atrial rate. The atrial rate may be determined from one or more A4-A4 event intervals determined just prior to switching to the non-atrial tracking mode. In this case, pacemaker 14 may operate in a temporary VDI pacing mode at a ventricular pacing rate set based on a previously determined A4 event rate. Control module 206 may set a temporary VDI pacing mode timer or enable a counter to count the number of ventricular pacing pulses delivered at the A4 event-based rate.

If no A4 event detections occur during this temporary VDI mode at a ventricular rate based on the A4 event rate, or pacing mode switching criteria remain unsatisfied at block 914, control mode 206 determines whether the temporary non-atrial tracking mode is expired at block 904. If the temporary mode timer is expired or a ventricular pacing pulse counter reaches a maximum temporary mode count, control module 206 may switch to a VDIR mode at block 905 during which the ventricular pacing rate is controlled by pacemaker 14 according to the programmed VDIR lower rate interval and an SIR transfer function for determining a SIR using a patient activity metric determined from the motion sensor signal. The ventricular pacing rate is no longer controlled based on the most recent A4 event rate and is controlled based on patient activity.

In this way, control module 206 switches to a first non-atrial tracking pacing mode for a predetermined time interval or number of ventricular cycles during which the ventricular pacing rate is based on the most recently determined atrial rate. If the temporary non-atrial tracking pacing mode is not expired (block 904), pacemaker 14 returns to block 902 and remains in the VDI pacing mode at the A4 rate-based ventricular pacing rate. For example, the pacing rate may be set to match the most recent A4 event rate or set to a rate that is at least 10 to 20 pulses per minute slower than the most recent A4 event rate.

When the temporary non-atrial tracking pacing mode expires at block 904, e.g., based on a predetermined time interval or maximum number of ventricular pacing pulses at the temporary A4 event rate-based pacing rate, control module 206 switches to a second, non-atrial tracking pacing mode at block 905. The second non-atrial tracking pacing mode may not have a time limit. The second non-atrial tracking pacing mode may extend for an indefinite time or number of ventricular cycles, until pacing mode switching criteria for switching back to the atrial-tracking pacing mode are satisfied. During the second, non-atrial tracking pacing mode the ventricular pacing rate is not based on a recent A4 event rate. The ventricular pacing rate during the second, non-tracking pacing mode may be based on a programmed VDI lower rate interval and/or SIR.

If an A4 event detection is not made at block 903 during the VDIR permanent LR interval or during a temporary LR interval set according to the SIR during the second non-atrial tracking pacing mode, control circuit 206 may extend the temporary (or permanent) LR interval currently in effect at block 910. The LR interval may be extended to promote A4 event detection between ventricular pacing pulses. The LR interval may be extended at block 910 if the control circuit 206 detects a decrease in SIR at block 906. Control circuit 206 may additionally or alternatively extend the LR interval periodically on a scheduled basis. Control circuit determines if it is time for a periodic check for A4 event detection at block 908 based on a scheduled frequency, which may be dependent on the SIR. For example, the LR interval may be extended every 16 pacing pulses to decrease the pacing rate by 10 ppm. The LR interval may be extended more frequently at a lower SIR than at a higher SIR. If an A4 event is detected during the extended LR interval (block 912), the extended LR interval may be applied for additional pacing cycles in order to determine if pacing mode switching criteria are satisfied at block 914. As given in the preceding examples, X of Y A4 event detection criteria may be applied at block 914 along with other optional criteria relating to motion sensor signal stability, patient body posture, patient physical activity level or SIR, or a motion signal metric determined as a running average or over a predetermined time interval. One or more other motion signal metrics may be determined and compared to respective thresholds for determining whether to switch back to the VDD pacing mode.

If the mode switching criteria are satisfied at block 914, control circuit 206 switches to the VDD pacing mode at block 916. If mode switching criteria are not satisfied, the LR interval is restored at block 918 from the extended LR interval applied at block 910. Pacemaker 14 remains in the VDIR pacing mode by returning to block 902.

Figure 14:
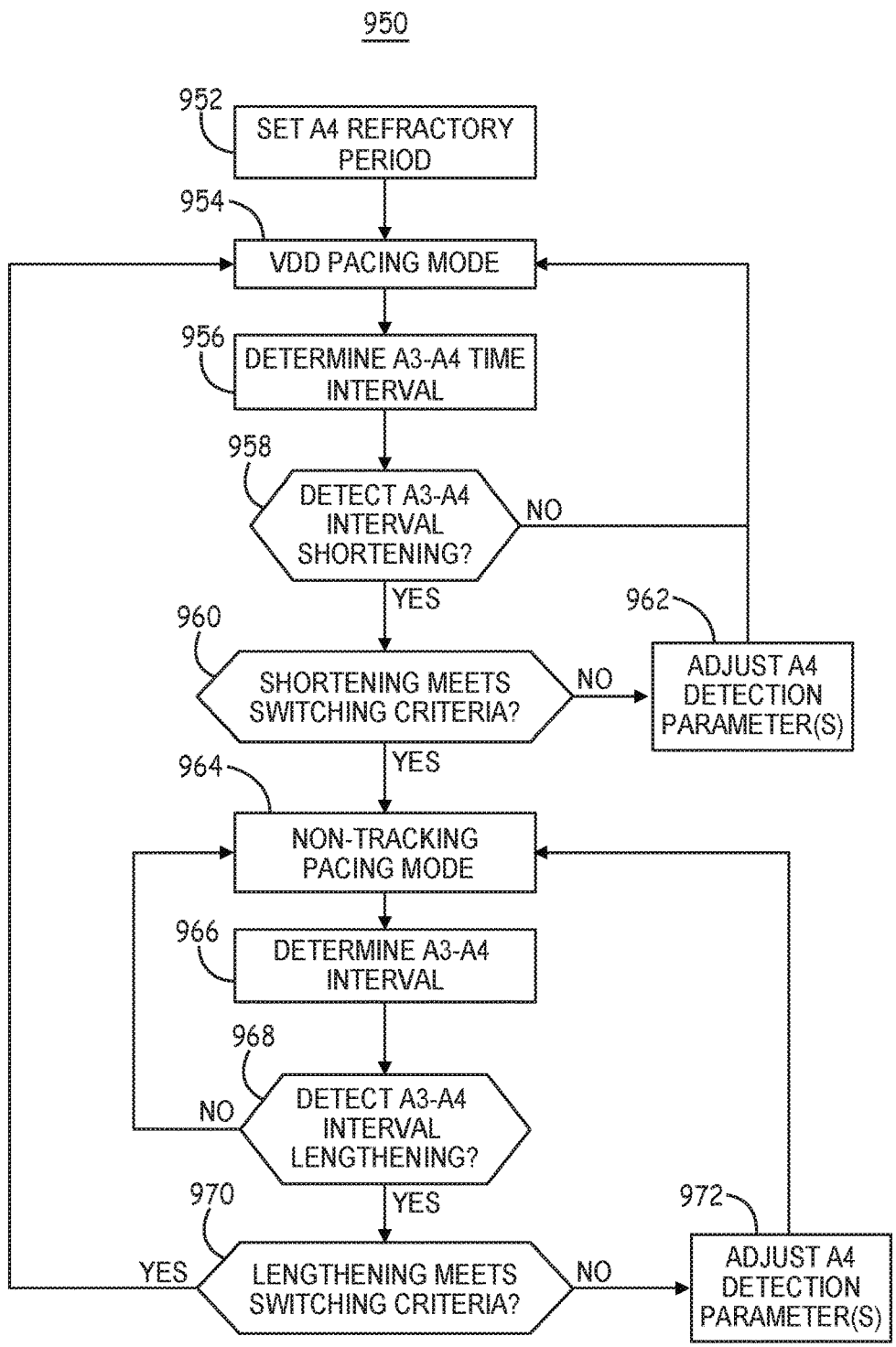
FIG. 14 is a flow chart of a method performed by a pacemaker for controlling pacing mode switching according to another example.

FIG. 14 is a flow chart 950 of a method performed by pacemaker 14 for controlling pacing mode switching according to another example. At block 952, the A4 refractory period is set, for example using any of the techniques described above in conjunction with FIGS. 5 through 8. At block 956, the A3 -A4 time interval is determined. The A3 -A4 time interval may be determined on a beat-by-beat basis or less frequently, for example every third beat, every fifth beat, etc. The A3 -A4 time interval may be used to update a running average A3 -A4 time interval stored in memory 210 and/or stored individually in a buffer in memory 210 storing a sequence of consecutive or non-consecutive A3 -A4 time intervals. In some examples, the A3 -A4 time interval may be determined as the time from the last, negative-going A3 threshold amplitude crossing to the first, positive-going A4 threshold amplitude crossing, e.g., A3 -A4 time interval 445 as shown in FIG. 6. In other examples, other fiducial points or threshold crossings of the A3 and A4 events may be used for determining an A3 -A4 time interval.

The A3 -A4 time interval determined at block 956 may additionally or alternatively be used as a motion signal metric for determining if mode switching criteria are met.

The A3 -A4 time interval may be compared to interval shortening criteria at block 958 to detect shortening of the A3 -A4 time interval by control circuit 206. The current A3 -A4 time interval may be compared to one or more previously determined A3 -A4 time intervals, individually or combined, e.g., as a running mean or median value. The ratio or difference of the current A3 -A4 time interval to or from the one or more previously determined A3 -A4 time intervals may be compared to a shortening threshold. In other examples, a decreasing trend in a running sequence of three or more A3 -A4 time intervals, consecutive or non-consecutive, may be detected as a shortening of the A3 -A4 time interval.

If a shortening of the A3-A4 time interval is detected at block 958, the amount of shortening is compared to pacing mode switching criteria at block 960. For example, a difference between the currently detected A3-A4 time interval and a preceding time interval or running average A3-A4 time interval may be compared to a switching threshold at block 960. If pacing mode switching criteria are not met, one or more A4 detection control parameters may be adjusted in response to detecting the A3-A4 time interval shortening at block 962. The A4 refractory period may be shortened and/or the A4 detection threshold amplitude may be adjusted. For example the A4 detection threshold amplitude may be adjusted to enable detection of fused A3-A4 events. Early detection of the A4 event during the A4 refractory period may be enabled or other adjustments of the A4 detection control parameters may be made, e.g., as generally disclosed in U.S. patent application Ser. No. 15/280,538 (Sheldon, et al., filed on Sep. 29, 2016), U.S. patent application Ser. No. 15/280,339 (Splett, et al., filed on Sep. 29, 2016) and in U.S. patent application Ser. No. 15/342,699 (Demmer et al.,) all of which are incorporated herein by reference in their entirety. The ventricular pacing mode remains in the VDD pacing mode at block 954.

If the A3 -A4 time interval shortening meets pacing mode switching criteria at block 960, control circuit 206 switches to a non-tracking pacing mode at block 964, e.g., VVIR or VDIR pacing. The control circuit 206 may continue monitoring the A3-A4 time interval at block 966 while operating in the non-atrial tracking pacing mode. A3 -A4 time intervals may be determined beat-by-beat during the VDIR pacing mode or be determined periodically during the VVIR or VDIR pacing modes. If A3 -A4 time interval lengthening is detected at block 968, the increase in the A3 -A4 time interval may be compared to pacing mode switching criteria at block 970. If pacing mode switching criteria are met at block 970, control circuit 206 may switch back to the VDD pacing mode at block 954. If the A3 -A4 time interval becomes greater than a threshold time interval, or the A3 -A4 time interval presents an increasing trend, a return of reliable A4 detection is expected so that VDD pacing may be restored. Other mode switching criteria described herein may also be applied at block 970 in other examples.

If lengthening of the A3 -A4 time interval does not meet pacing mode switching criteria at block 970, pacemaker 14 remains in the non-atrial tracking pacing mode at block 964. In some examples, an increase in the A3 -A4 time interval may result in an adjustment of the A4 refractory period, A4 detection threshold amplitude or other A4 detection control parameter or combination of A4 detection control parameters at block 972.

Operations performed in the method of flow chart 950 may be performed in combination with any of the techniques described in conjunction with FIGS. 9, 10A, 10B, 11, 12 and 13 for controlling pacing mode switching. As such, in some examples, any other pacing mode switching criteria described herein may be applied at blocks 960 and/or 970 in addition to detecting a change in the A3 -A4 time interval before switching the pacing mode.

Thus, various methods for controlling pacing mode switching in an intracardiac ventricular pacemaker configured to deliver ventricular pacing in an atrial tracking and in a non-atrial tracking pacing mode have been described according to illustrative embodiments. In other examples, various methods described herein may include steps performed in a different order or combination than the illustrative examples shown and described herein. Furthermore, other circuitry may be conceived by one of ordinary skill in the art for implementing the techniques disclosed herein; the particular examples described herein are illustrative in nature and not intended to be limiting. It is appreciated that various modifications to the referenced examples may be made without departing from the scope of the disclosure and the following claims.

The invention claimed is:

1. An intracardiac ventricular pacemaker, comprising:
a pulse generator configured to generate and deliver pacing pulses to a ventricle of a patient's heart via electrodes coupled to the pacemaker;
a motion sensor configured to produce a motion signal; and
a control circuit configured to receive the motion signal and communicate with the pulse generator, the control circuit configured to:
detect atrial systolic events from the motion signal;
operate in a selected one of an atrial-tracking ventricular pacing mode and a non-atrial tracking ventricular pacing mode;
while operating in the selected one of the atrial-tracking ventricular pacing mode and the non-atrial tracking ventricular pacing mode, determine at least one motion signal metric based on a rate of at least some of the detected atrial systolic events;
determine a patient physical activity metric from the motion signal;
set a pacing mode switching threshold based on the patient physical activity metric;
compare the at least one motion signal metric to the pacing mode switching threshold; and
responsive to the pacing mode switching threshold being satisfied, switch from the selected one of the non-atrial tracking pacing mode and the atrial tracking pacing mode to the other one of the non-atrial tracking pacing mode and the atrial tracking pacing mode for controlling the pacing pulses delivered by the pulse generator.

2. The pacemaker of claim 1, wherein the the at least one motion signal metric is further based on the patient physical activity metric determined from from the motion signal.

3. The pacemaker of claim 1, wherein the rate of the at least some of the detected atrial systolic events comprises a count of the at least some of the detected atrial systolic events.

4. The pacemaker of claim 1, wherein the control circuit is configured to:
determine a patient posture from the motion signal; and
wherein the at least one motion signal metric is further based on the patient posture.

5. The pacemaker of claim 1, wherein the control circuit is configured to determine the at least one motion signal metric by processing the motion signal over a predetermined time segment.

6. The pacemaker of claim 1, wherein the control circuit is configured to:
extend a ventricular pacing rate interval for at least one ventricular cycle;
detect an atrial systolic event from the motion signal during the extended ventricular pacing rate interval; and
determine if the pacing mode switching threshold are met in response to detecting the atrial systolic event.

7. The pacemaker of claim 6, wherein:
the pacemaker further includes a sensing circuit for receiving a cardiac electrical signal via electrodes coupled to the pacemaker;
the control circuit is further configured to:
detect at least one of:
a premature ventricular contraction from the cardiac electrical signal,
a decreased patient physical activity from the motion signal, and
a change in patient body posture from the motion signal; and
extend the ventricular pacing rate interval in response to detecting at least one of the premature ventricular contraction, the decreased patient physical activity, and the change in patient posture.

8. The pacemaker of claim 6, wherein the control circuit is further configured to:
periodically extend the ventricular pacing rate interval at a frequency that is dependent on the patient physical activity metric.

9. The pacemaker of claim 1, wherein the control circuit is further configured to:
determine a patient condition from the motion signal; and
set the pacing mode switching threshold based on the patient condition.

10. The pacemaker of claim 1, wherein the control circuit is configured to:
determine a first motion signal metric from the motion signal;
compare the first motion signal metric to a first pacing mode switching criterion;
determine a second motion signal metric from the motion signal;
compare the second motion signal metric to a second pacing mode switching criterion; and
switching the pacing mode in response to the first and the second pacing mode switching criterion being satisfied.

11. The pacemaker of claim 1, wherein the control circuit is further configured to:
detect a plurality of the atrial systolic events from the motion signal; and
determine the at least one motion signal metric by determining a stability of the plurality of atrial systolic events.

12. The pacemaker of claim 1, where in the control module is further configured to:
switch from the atrial tracking pacing mode to a first non-atrial tracking pacing mode for a temporary interval; and
switch from the first non-atrial tracking pacing mode to a second non-atrial tracking pacing mode in response to the temporary interval expiring.

13. The pacemaker of claim 1, further comprising:
a housing enclosing the pulse generator, the motion sensor, and the control circuit; and at least one electrode carried by the housing and coupled to the pulse generator for delivering the ventricular pacing pulses.

14. The pacemaker of claim 1, wherein the control circuit is configured to:
switch from the atrial-tracking ventricular pacing mode to the non-atrial tracking pacing mode in response to the rate of the detected atrial systolic events being less than the pacing mode switching threshold.

15. An intracardiac ventricular pacemaker comprising:
a pulse generator configured to generate and deliver pacing pulses to a ventricle of a patient's heart via electrodes coupled to the pacemaker;
a motion sensor configured to produce a motion signal; and
a control circuit configured to receive the motion signal and communicate with the pulse generator, the control circuit configured to:
detect an atrial systolic event from the motion signal;
detect a ventricular diastolic event from the motion signal;
operate in a selected one of an atrial-tracking ventricular pacing mode and a non-atrial tracking ventricular pacing mode;
while operating in the selected one of the atrial-tracking ventricular pacing mode and the non-atrial tracking ventricular pacing mode, determine at least one motion signal metric based on a time interval from the ventricular diastolic event to the atrial systolic event;
compare the at least one motion signal metric to pacing mode switching criteria; and
responsive to the pacing mode switching criteria being satisfied, switch from the selected one of the non-atrial tracking pacing mode and the atrial tracking pacing mode to the other one of the non-atrial tracking pacing mode and the atrial tracking pacing mode for controlling the pacing pulses delivered by the pulse generator.

16. A method performed by an intracardiac ventricular pacemaker having a motion sensor configured to produce a motion signal, the method comprising:
detecting atrial systolic events from the motion signal;
operating in a selected one of an atrial-tracking ventricular pacing mode and a non-atrial tracking ventricular pacing mode;
while operating in the selected one of the atrial-tracking ventricular pacing mode and the non-atrial tracking ventricular pacing mode, determining by a control circuit of the pacemaker at least one motion signal metric based on a rate of at least some of the detected atrial systolic events;
determining a patient physical activity metric from the motion signal;
setting a pacing mode switching threshold based on the patient physical activity metric;
comparing the at least one motion signal metric to pacing mode switching criteria,
wherein the comparing comprises comparing the rate of the at least some of the detected atrial systolic events to the pacing mode switching threshold; and
responsive to the pacing mode switching criteria being satisfied, switching from the selected one of the non-atrial tracking pacing mode and the atrial tracking pacing mode to the other one of the non-atrial tracking pacing mode and the atrial tracking pacing mode for controlling ventricular pacing pulses delivered by the pacemaker.

17. The method of claim 16, wherein the at least one motion signal metric is further based on the patient physical activity metric.

18. The method of claim 16, wherein the rate of the at least some of the detected atrial systolic events comprises a count of the at least some of the detected atrial systolic events.

19. The method of claim 16, further comprising determining a patient posture from the motion signal, and wherein the at least one motion signal metric is further based on the patient posture.

20. The method of claim 16, wherein determining the at least one motion signal metric comprises processing the motion signal over a predetermined time segment.

21. The method of claim 16, further comprising:
extending a ventricular pacing rate interval for at least one ventricular cycle;
detecting an atrial systolic event from the motion signal during the extended ventricular pacing rate interval; and
determining if the pacing mode switching criteria are met in response to detecting the atrial systolic event.

22. The method of claim 21, further comprising:
detecting by the control circuit at least one of:
a premature ventricular contraction from a cardiac electrical signal received by a sensing circuit of the pacemaker,
a decreased patient physical activity from the motion signal, and
a change in patient body posture from the motion signal; and
extending the ventricular pacing rate interval in response to detecting at least one of the premature ventricular contraction, the decreased patient physical activity, and the change in patient posture.

23. The method of claim 21, further comprising:
periodically extending the ventricular pacing rate interval at a frequency that is dependent on the patient physical activity metric.

24. The method of claim 16, further comprising:
determining a patient condition from the motion signal; and
setting, by the control circuit, the pacing mode switching criteria based on the patient condition.

25. The method of claim 16, further comprising:
determining a first motion signal metric from the motion signal;
comparing the first motion signal metric to a first pacing mode switching criterion;
determining a second motion signal metric from the motion signal;
comparing the second motion signal metric to a second pacing mode switching criterion; and
switching the pacing mode in response to the first pacing mode switching criterion and the second pacing mode switching criterion being satisfied.

26. The method of claim 16, further comprising:
detecting a plurality of the atrial systolic events from the motion signal; and
determining the at least one motion signal metric by determining a stability of the plurality of atrial systolic events.

27. The method of claim 16, wherein in switching from the atrial tracking pacing mode to the non-atrial tracking pacing mode comprises:
  switching from the atrial tracking pacing mode to a first non-atrial tracking pacing mode for a temporary interval; and
  switching from the first non-atrial tracking pacing mode to a second non-atrial tracking pacing mode in response to the temporary interval expiring.

28. The method of claim 16, further comprising delivering the ventricular pacing pulses via at least one electrode carried by a housing that encloses the pulse generator, the motion sensor, and the control circuit of the pacemaker.

29. A method performed by an intracardiac ventricular pacemaker having a motion sensor configured to produce a motion signal, the method comprising:
  detecting a ventricular diastolic event from the motion signal;
  detecting an atrial systolic event from the motion signal;
  operating in a selected one of an atrial-tracking ventricular pacing mode and a non-atrial tracking ventricular pacing mode;
  while operating in the selected one of the atrial-tracking ventricular pacing mode and the non-atrial tracking ventricular pacing mode, determining the at least one motion signal metric based on a time interval from the ventricular diastolic event to the atrial systolic event;
  comparing the at least one motion signal metric to pacing mode switching criteria; and
  responsive to the pacing mode switching criteria being satisfied, switching from the selected one of the non-atrial tracking pacing mode and the atrial tracking pacing mode to the other one of the non-atrial tracking pacing mode and the atrial tracking pacing mode for controlling ventricular pacing pulses delivered by the pacemaker.

* * * * *